US012618841B2

(12) United States Patent  (10) Patent No.: US 12,618,841 B2
Rabizadeh  (45) Date of Patent: May 5, 2026

(54) METHODS OF DIAGNOSING MALIGNANT DISEASES

(71) Applicant: ST INNOVATIVE DIAGNOSTICS LTD, Be'er Yaakov (IL)

(72) Inventor: Esther Rabizadeh, Be'er Yaakov (IL)

(73) Assignee: ST INNOVATIVE DIAGNOSTICS LTD, Be'er Yaakov (IL)

( * ) Notice: Subject to any disclaimer, the term of this patent is extended or adjusted under 35 U.S.C. 154(b) by 15 days.

(21) Appl. No.: 18/074,479

(22) Filed: Dec. 4, 2022

(65) Prior Publication Data

US 2023/0109120 A1     Apr. 6, 2023

Related U.S. Application Data

(62) Division of application No. 16/480,342, filed as application No. PCT/IB2018/050454 on Jan. 24, 2018, now Pat. No. 11,519,914.

(60) Provisional application No. 62/450,082, filed on Jan. 25, 2017.

(51) Int. Cl.
　　*G01N 33/86*　　　(2006.01)
　　*G01N 33/574*　　 (2006.01)

(52) U.S. Cl.
　　CPC ........... *G01N 33/574* (2013.01); *G01N 33/86* (2013.01); *G01N 2333/75* (2013.01); *G01N 2333/974* (2013.01); *G01N 2800/52* (2013.01)

(58) Field of Classification Search
　　None
　　See application file for complete search history.

(56) References Cited

U.S. PATENT DOCUMENTS

| | | | |
|---|---|---|---|
| 9,023,609 B2 | 5/2015 | Inbal et al. | |
| 2008/0026447 A1* | 1/2008 | Blat .......................... | C12Q 1/56 435/219 |

FOREIGN PATENT DOCUMENTS

| | | | |
|---|---|---|---|
| WO | WO2012007940 | 1/2012 | |
| WO | WO-2012007940 A1 * | 1/2012 | ............... C12Q 1/37 |

OTHER PUBLICATIONS

Sherman et al., Acta Derm Venereol., Mar. 10, 2017;97(3):370-372. doi: 10.2340/00015555-2514. Epub Aug. 18, 2016.*
Tang et al., Hum Pathol. Aug. 2009;40(8):1194-9. doi: 10.1016/j.humpath.2009.02.011. Epub May 8, 2009. PMID: 19427022.*
Extended European Search Report and Written Opinion for uropean Application No. 18744481.5, mailed Sep. 7, 2020.
International Preliminary Report on Patentability for International Application No. PCT/IB2018/050454, mailed Aug. 8, 2019.
International Search Report and Written Opinion for International Application No. PCT/IB2018/050454, mailed May 17, 2018.
Melnyk, M. C., Shalev, I., Zhang, J., Bartczak, A., Gorczynski, R. M., Selzner, N., . . . & Levy, G. A. (2011). The prothrombinase activity of FGL2 contributes to the pathogenesis of experimental arthritis. Scandinavian journal of rheumatology, 40(4), 269-278.
Rabizadeh E., et al., "Increased Activity of Cell Membrane-Associated Prothrombinase, Fibrinogen-Like Protein 2, in 5 Peripheral Blood Mononuclear Cells of B-Cell Lymphoma Patients," Public Library of Science One, Oct. 10, 2014, vol. 9(10), e109648, 5 pages.
Rabizadeh E., et al., Abstract only, "Fibrinogen-Like Protein 2 (FGL2) Activity in Platelets—Implication for Novel Cancer DI-Agnostic and Follow Up Approaches," International Journal of Laboratory Hematology, 2017, vol. 39(2), pp. 3-133.
Rabizadeh E., et al., Abstract only, "PB2216: Elevated Activity of Fibrinogen-Like Protein 2 (FGL2/fibroleukin) Platelets From Cancer Patients," International Society on Thrombosis and Haemostasis (ISTH), Jul. 1, 2017, vol. 1(1), p. 1280.
Sherman S., et al., "Fibrinogen-Like Protein 2 Activity as a Potential Biomarker for Diagnosis of Early Mycosis Fungoides," Acta Dermato-Venereologica, 2017, vol. 97, pp. 370-372.
Su K., et al., "Fibrinogen-like Protein 2/Fibroleukin Prothrombinase Contributes to Tumor Hypercoagulability via IL-2 and IFN-y," World Journal of Gastroenterology, Oct. 21, 2008, vol. 14(39), pp. 5980-5989.

* cited by examiner

Primary Examiner — Michael Szperka

(74) Attorney, Agent, or Firm — Mark S. Cohen; PEARL COHEN ZEDEK LATZER BARATZ LLP

(57) ABSTRACT

A method for diagnosing a malignant proliferative disease or disorder in a subject, and/or for following up, monitoring or prognosticating the therapy of a malignant proliferative disease or disorder in a subject is disclosed. The method is based on measurement of platelet-mediated fibrinogen-like protein 2 (FGL2) activity in a sample essentially comprising platelets obtained from the subject. In accordance with the disclosed method, platelet-mediated FGL2 activity level higher than control is indicative of the presence of a malignant proliferative disease or disorder in a subject.

16 Claims, 10 Drawing Sheets

Fig. 7A
Fig. 7B
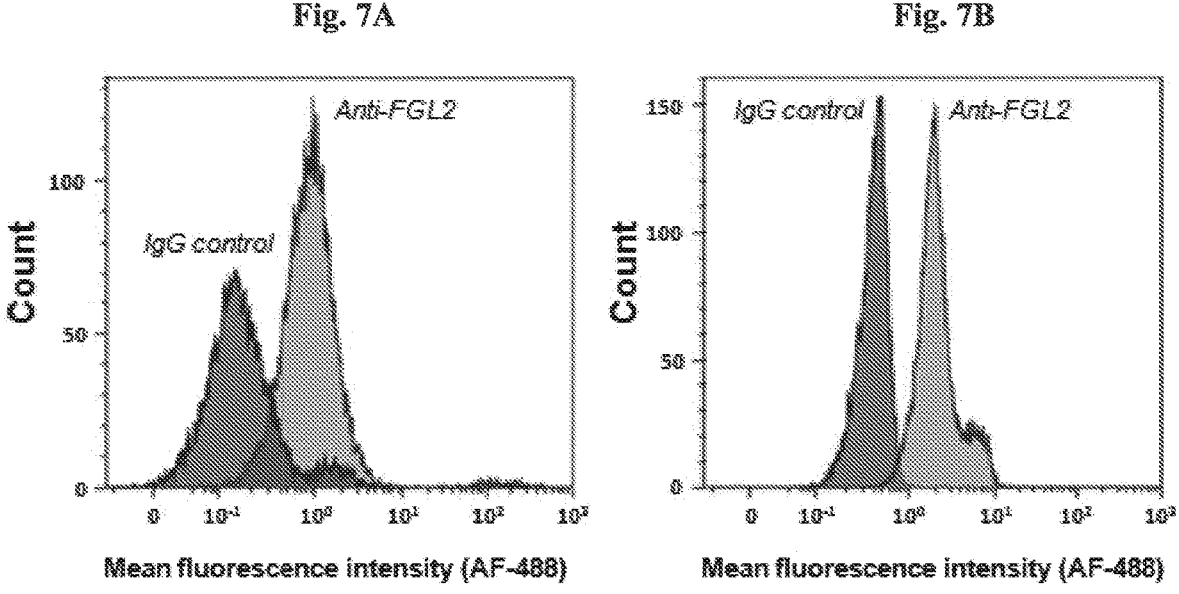
Fig. 7C
Fig. 7D
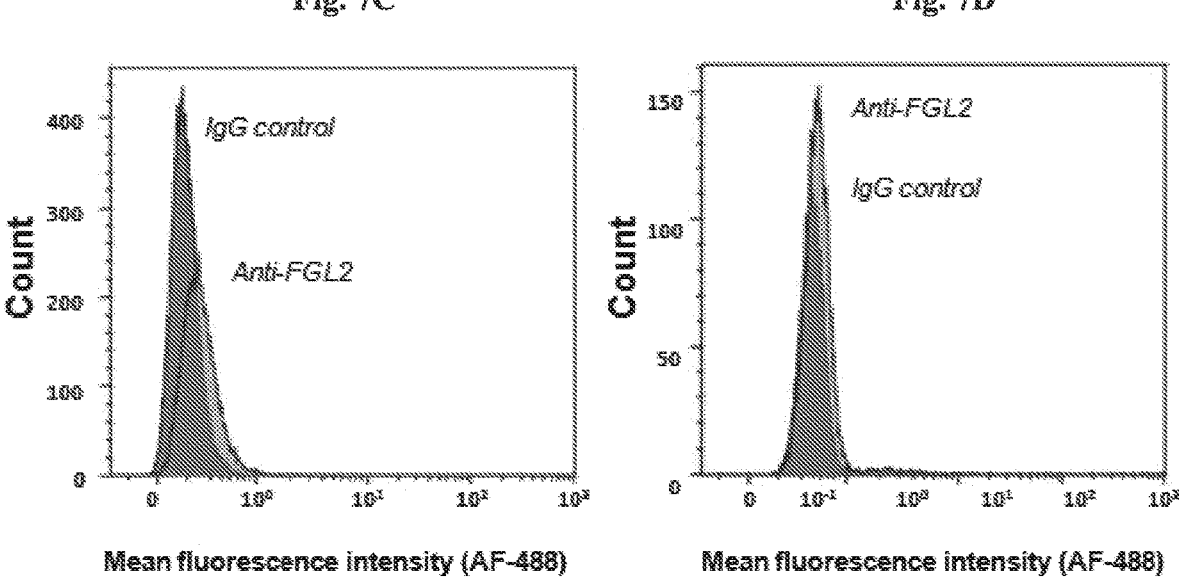

METHODS OF DIAGNOSING MALIGNANT DISEASES

FIELD AND BACKGROUND OF THE INVENTION

The present invention relates, at least in part, to methods of diagnosing and monitoring a malignant disease based on fibrinogen-like protein 2 activity.

The fibrinogen like protein 2 (FGL2), also known as fibroleukin is a member of the fibrinogen-related protein superfamily that shares high conservation among different species. The human gene is approximately 7 kb in length with 2 exons. From the nucleotide sequence of the human gene, a 439-amino acid long protein is predicted.

Thrombosis and inflammation are regulated by an assortment of proteins and cells that contribute to the pathophysiology of the pathways. Fibrinogen-like protein 2 is considered a prominent player in this axis, exhibiting multiple functions that are involved in normal and pathological processes, thereby serving as an important mediator of immune coagulation and inflammation.

Fibrinogen-like protein 2 encompasses two structurally and functionally distinct forms. A soluble form FGL2 (sFGL2), expressed and secreted by regulatory T cells (peripheral blood CD4$^+$ and CD8$^+$ T cells). Soluble FGL2 lacks the N-terminal region (~50 kDa) and possesses significant immunosuppressive properties while considered to be deficient of procoagulant activity.

The membrane-bound form of FGL2 (mFGL2), also referred to herein as "FGL2 prothrombinase", contains the N-terminal region (~65 kDa) and possesses procoagulant activity. It is a serine protease capable of directly cleaving prothrombin into thrombin while bypassing the canonical coagulation route. The mFGL2 form has been reported to be mainly expressed on the surface of macrophages, dendritic cells, endothelial cells, epithelial cells and cancer cells. Interestingly, mFGL2 procoagulant activity has been reported to be exerted mainly in response to pathologic stimuli, while the soluble form (sFGL2) is expressed and secreted constitutively by lymphocytes. Membrane-bound FGL2 does not need to be cleaved to be activated, it leads to fibrin deposition in the absence of factor VII or factor X, and triggers thrombosis, however, it still requires Factor Va, calcium and phospholipids to reach its maximal enzymatic activity.

The importance of mFGL2 is manifested by the range of functions and applications that were ascribed to it. This protein plays a key role in various biological processes including embryonic development and miscarriage, microthrombosis, inflammatory immuno-response, viral infection and fulminant hepatitis, ischemia/reperfusion injury, allograft rejection and tumorigenesis.

An increase in FGL2 protein and FGL2 mRNA expression has been observed in various types of solid tumors, while the normal tissue surrounding the tumor did not display overexpression of FGL2 as observed in the tumor itself, and it has been suggested the FGL2 has a role in tumor progression (Su, K. et al. (2008) World J. Gastroenterol. 14(39): 5980-5989). Fibrinogen-like protein 2 in tumor cells and milieu may affect tumor development via several proposed possible mechanisms, such as enhancement of tumor cell proliferation, induction of angiogenesis and metastasis, activation of MAPK pathway, promotion of immune suppression, and generation of thrombin leading to thrombin-mediated tumorigenesis.

Despite the biological availability of active FGL2 prothrombinase in the blood, there is no published data regarding the precise origin and significance of this active procoagulant form in peripheral blood cells (PBC).

Platelets have multipurpose roles and a significant influence on hemostasis, inflammation, infection, immunity and malignant diseases. Hemostasis is considered the primary role of platelets. Beyond aggregation, activated platelets provide the phosphatidylserine phospholipid surfaces upon which the complex reactions of the blood coagulation cascade are localized. Platelets further store and secret coagulation factors and co-factors including factors V, XI, XIII, prothrombin (in their inactive forms), high molecular weight kininogens and polyphosphates. The pathophysiologic role of platelets in tumor development is well recognized (see, for example, Franco et al., *Blood,* 126:582-588, 2015; Golebiewska and Poole, *Blood Rev.,* 29:153-162, 2015).

SUMMARY

This disclosure is directed, at least in part, to a method for diagnosing a malignant proliferative disease or disorder in a subject, comprising the steps of: (a) obtaining a biological sample containing platelets of the subject; (b) inducing platelet-mediated fibrinogen-like protein 2 (FGL2) activity in the biological sample; (c) measuring the FGL2 activity level in the sample; and (d) comparing the measured FGL2 activity level with that of a control value, whereby a sample with platelet-mediated FGL2 activity level higher than control is indicative of the presence of a malignant proliferative disease or disorder in a subject.

This disclosure is further directed to a method for prognosis, follow up or monitoring the therapy of a malignant proliferative disease or disorder in a subject, the method comprising the steps of: (a) obtaining a biological sample containing platelets of the subject; (b) inducing platelet-mediated FGL2 process in the biological sample; (c) measuring the platelet-mediated FGL2 activity level in the sample at different time points in the course of a treatment protocol for a malignant proliferative disease or disorder, for example, at one or more time points before application of a treatment protocol, one or more time points during the course of a treatment protocol, and/or one or more time points after end of a treatment protocol; and (d) comparing the measured platelet-mediated FGL2 activity level with that of a control value and/or with a previous time point value, whereby increasing platelet-mediated FGL2 activity over time indicates a poor prognosis or resistance to therapy of said malignant proliferative disease or disorder, whereas a decreasing platelet-mediated FGL2 activity over time indicates recovery or cure of the subject.

In some embodiments, the platelet-mediated FGL2 activity utilized in a disclosed method is coagulation activity or fibrin generation, which may be induced in step (b) by addition of, for example, Factor X deficient plasma (FXDP) and tissue factor, and measured in step (c) based on, for example, measuring platelet-mediated FGL2 coagulation time (CT).

In some embodiments, the platelet-mediated FGL2 activity utilized in a disclosed method is thrombin generation or prothrombinase activity, which may be induced in step (b) by addition of an FGL2 prothrombinase substrate such as a chromogenic substrate, prothrombin, a prothrombin derivative, a prothrombin analog, or any combination thereof. Measurement, in step (c), of the platelet-mediated FGL2 thrombin generation or prothrombinase activity level may be based on, for example, measuring platelet-mediated FGL2 units or concentrations of generated thrombin.

The control value in a disclosed method may be, for example, the platelet-mediated FGL2 activity level in a subject not affected by a malignant proliferative disease.

In some embodiments, step (a) of a disclosed method may further comprise maintaining a predetermined count of platelets in the biological sample, for example, in a range of from about $1\times10^6$ to about $1000\times10^6$ platelets per sample. In some exemplary embodiments the biological sample contains platelets count of about $100\times10^6$ platelets per sample.

In some embodiments, step (b) of a disclosed method may further comprises lysis of the cells in the sample.

The biological sample containing platelets utilized in a disclosed method may be pure platelets, a platelet-rich plasma (PRP) or peripheral blood cells (PBC) supplemented with platelets obtained from the subject.

A malignant proliferative disease or disorder that may optionally be diagnosed and/or the course of treatment thereof may optionally be monitored, followed-up and/or prognosticated utilizing a disclosed method, may be a solid tumor or a non-solid malignancy for example a hematological malignancy such as mycosis fungoides (MF), Sézary syndrome or an aggressive lymphoma.

This disclosure is further directed to a kit for diagnosis, follow-up or prognosis of a malignant proliferative disease or disorder, the kit comprising: (a) at least one reagent for measuring platelet-mediated FGL2 activity level; (b) instructions for measuring platelet-mediated FGL2 activity level in a sample; and, optionally, (c) at least one means for collecting a sample to be tested; and/or (d) at least one control sample.

A disclosed kit may be designed for assessing e.g., platelet-mediated FGL2 coagulation activity level, platelet-mediated FGL2 units (namely FGL2 protein associated with platelets) or thrombin concentration.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. It is stressed that the particulars shown in the drawings are by way of example and for purposes of illustrative discussion of embodiments of the invention. In this regard, the description taken with the drawings makes apparent to those skilled in the art how embodiments of the invention may be practiced.

In the drawings:

FIG. 1A shows the correlation between coagulation time and thrombin generation analysis. Linear regression correlation coefficient r=−0.64. FIG. 1B shows correlation between coagulation time and platelet count. Power regression correlation coefficient r=0.72;

FIG. 2A: samples containing $58\times10^6$ platelets and increasing amounts of white blood cells ($0.03\text{-}2\times10^6$). FIG. 2B: samples containing similar white blood cells counts ($1.6\text{-}2\times10^6$) and increasing amounts of platelets ($0\text{-}1.5\times10^6$);

FIG. 4A is a Western blot analysis of FGL2 in $1\times10^6$ PC3 cells extract, wild type and FGL2 overexpressing strain. FIG. 4B is a bar graph showing mean coagulation times of FXDP in the presence of $1\times10^6$PC3 cells extracts (wild type or overexpressing FGL2). Experiments were performed in triplicates. *P-value=0.01;

FIGS. 7A-7D are flow cytometry histograms showing the detection of FGL2 in permeabilized platelets and lymphocytes (FIG. 7A, and FIG. 7C, respectively), and non-permeabilized (intact) platelets and lymphocytes (FIG. 7B, and FIG. 7D, respectively). The fluorescence intensity of IgG control-Alexa Fluor® 488 (Red) or FGL2-Alexa Fluor® 488 (Green) antibodies was detected in gated platelet using log SSC/FSC/CD41$^+$ or in gated lymphocyte using CD45$^+$/SSC;

DESCRIPTION OF SPECIFIC EMBODIMENTS OF THE INVENTION

Figure 1A:
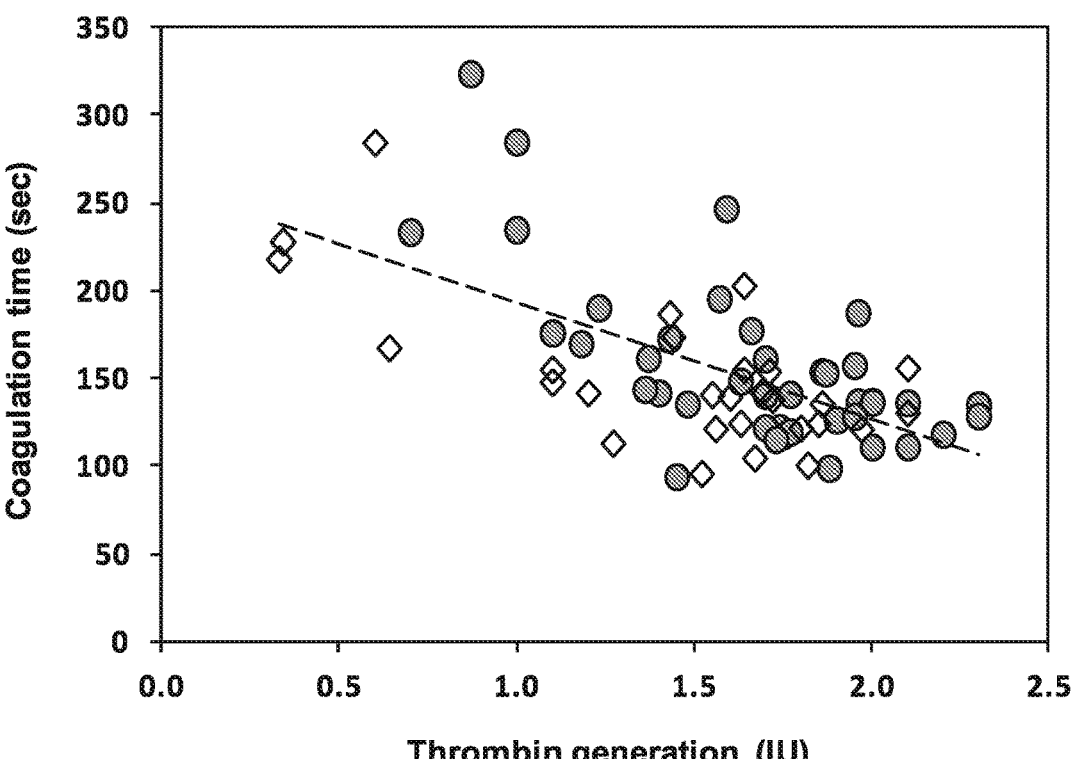
FIGS. 1A-1B are graphs showing analysis of coagulation time in peripheral blood cell samples from healthy individuals (full circles) and hospitalized patients with viral or bacterial infections (empty rhombuses).

The present invention relates, at least in part, to methods of diagnosing and monitoring a malignant disease based on fibrinogen-like protein 2 activity.

It is to be understood that the invention as described herein is not necessarily limited in its application to the details set forth in the following description or exemplified by the Examples. The invention is capable of other embodiments or of being practiced or carried out in various ways.

The present inventors envisaged monitoring FGL2 activity level, more specifically FGL2 procoagulant activity level, as a malignancy biomarker. They hypothesized that the elevated procoagulant activity reported in tumor cells and the interstitial milieu (infiltrated immune cells and vascular endothelium cells) (Su et al., *World J. Gastroenterol.* 14:5980-5989, 2008), may be accompanied by a systemic response, including an overall increase in procoagulant potent FGL2 activity manifested in blood samples.

Despite the biological availability of procoagulant active FGL2 prothrombinase in the blood, there is no specific data regarding the precise origin and significance of this active procoagulant form in peripheral blood. The majority of available data concerning the procoagulant activity of FGL2 from blood cells is related to macrophages in the tissues, while the origin of FGL2 procoagulant activity in blood samples extracts has been mistakenly exclusively ascribed to mononuclear cells.

The present inventors have elucidated an association between platelets and FGL2, and have shown, as described in the Examples section disclosed herein, that the coagulation activity measured in plasma-free PBC and platelet-rich plasma (PRP) samples is directly correlated with the number of platelets in a tested sample. Moreover, the present inventors have identified an active membrane-bound FGL2 in platelets cytoplasm and have established that coagulation time in a sample comprising platelets taken from a subject correlates with the level of FGL2 coagulation activity in the subject.

Example 1 herein discloses that the level of platelet-mediated FGL2 activity is the same both in healthy subjects and in patients diagnosed with viral or bacterial infections. This suggests that the FGL2 activity in platelets is not related to infection diseases and could be only the result of malignancy. Example 4 herein discloses that FGL2 is localized in the cytoplasm of resting platelets. Example 3 herein discloses that FGL2 is the major prothrombinase existing in platelets, and Example 6 herein discloses that FGL2 is responsible for mediating the procoagulant activity measured in PBC samples (that unavoidably contain platelets) or PRP sample. Overall, platelet-associated FGL2 is the major prothrombinase agent beyond the plasma Factor X in the blood.

Moreover, the present inventors have shown that, essentially, increased platelet-mediated FGL2 activity as compared to a given control is indicative of the presence of a malignant proliferative disorder in said subject, whereas platelet-mediated FGL2 activity in a subject inflicted with a non-malignant proliferative disease or disorder, for example a benign proliferative disorder, is comparable to FGL2 coagulation activity levels in a healthy subject (see Example 7 herein). Thus, it has been demonstrated by the present inventors that high platelet-mediated FGL2 coagulation activity correlates with malignancy.

Furthermore, as shown herein, when the platelet-mediated FGL2 activity remains high or increases over time in a subject inflicted with a malignant disease, it is an indication of resistance to therapy. In counterpart, a decrease in platelet-mediated FGL2 activity over time relative to the previous measurement during active malignant disease, indicates recovery or improvement of the disease. Correspondingly, an increase in platelet-mediated FGL2 activity over time relative to the previous measurement during remission of the disease indicates a relapse of the malignant disease.

Moreover, as disclosed in Example 8 herein, the ability of platelet-mediated FGL2 coagulation activity, observed in patients during the course of an anti-cancer treatment, to be predictive of the response of these patients to treatment and predictive of the disease state, was confirmed by positron-emission tomography (PET) scans. Being in high correlation with scanning- and imagine-based diagnostic techniques, platelet-mediated FGL2 activity may provide a straight forward, low cost and patient-friendly means to assist in treatment follow-up and monitoring, as well as in prognosis, particularly during the long intervals (which may last 6 months or more) between scanning and/or imaging episodes.

The present inventors have designed and successfully practiced a method of detecting and estimating the presence and stage of a malignant disease in a subject, utilizing platelets as a diagnostic marker for the presence of a malignant process in the subject. The method does not require use of expensive substrates and relies on semi-automated devices for assessing platelet-mediated, FGL2-induced coagulation time using a simple blood test. A contemplated diagnosis procedure based on platelet-mediated FGL2 coagulation activity, also termed herein the "platelet-assay", can be completed in approximately 45 minutes. The platelet assay is, thus, far more rapid than other, known assays, cost effective and suited for mass-scale screening, as required in large diagnostic facilities and hospitals. Platelets have not been utilized thus far for estimation of FGL2 coagulation levels.

U.S. Pat. No. 9,023,609 to the present inventors discloses a method of diagnosis and monitoring of a malignant proliferative disorder based on the level (i.e., concentration) of FGL2 prothrombinase in PMBC as determined by a thrombin generation (TG) assay, which necessitated use of purified prothrombin (FGL2 enzyme substrate) and a chromogenic substrate. These reagents were relatively expensive when used in mass-scale screening tests. Furthermore, the TG assay was both substantially longer than platelet-assay described herein and less accurate.

In an aspect of the disclosure, provided herein is a method for diagnosing a malignant proliferative disease or disorder in a subject, the method comprising the steps of: (a) obtaining a biological sample essentially containing platelets of the subject; (b) inducing platelet-mediated fibrinogen-like protein 2 (FGL2) activity in the biological sample; (c) measuring the FGL2 activity level in the sample; and (d) comparing the measured FGL2 activity level with that of a control value, whereby a sample with platelet-mediated FGL2 activity level higher than control is indicative of the presence of a malignant proliferative disease or disorder in a subject.

Indication of the presence of a malignant disease or disorder applies for a detection of existing malignant disease in a subject for the first time, or for detection of recurrence or relapse of a malignant disease in a subject.

The contemplated platelet-assay may also be useful in monitoring the efficacy of cancer treatment. Monitoring the efficacy of treatment is essential for assessing prognosis of cancer treatment.

Hence, the diagnostic method described herein may be effected in a subject either before, during or after cancer treatment, and the analysis of the results obtained at each time point (the level of platelet-mediated FGL2 prothrombinase activity) be compared, e.g., to that in the normal population, and/or to that of the same subject before being affected by the malignant disease. When the pattern of FGL2 coagulation activity of a subject is the closest to that of the normal population (or to that of the subject when diagnosed as healthy or in remission), it indicates a successful treatment, whereas a high or increasing level of FGL2 coagulation activity may indicate poor prognosis, treatment failure, and/or relapse, depending on each case.

In a further aspect of the disclosure, provided herein is a method for prognosis, follow up or monitoring the therapy of a malignant proliferative disease or disorder in a subject, the method comprising the steps of: (a) obtaining a biological sample essentially containing platelets of the subject; (b) inducing platelet-mediated fibrinogen-like protein 2 (FGL2) process in the biological sample; (c) measuring the platelet-mediated FGL2 activity level in the sample at different time points in the course of a treatment protocol for a malignant proliferative disease or disorder; and (d) comparing the measured platelet-mediated FGL2 activity level with that of a control value and/or with a previous time point value, whereby increasing platelet-mediated FGL2 activity over time indicates a poor prognosis or resistance to therapy of said malignant proliferative disease or disorder, whereas a decreasing platelet-mediated FGL2 activity over time indicates recovery or cure.

The term "prognosis" as used herein is estimation of the likely course and outcome of the disease. Prognosis of a malignant disease such as cancer usually means the estimate of success with treatment and chances of recovery. Prognosis is also predicting the likelihood of a person's survival. Accordingly, "poor prognosis" implies low chances of survival, low chances of recovery and/or failure of treatment.

In some embodiments, the platelet-mediated FGL2 activity being measured in a contemplated method is fibrin generation, clot formation or coagulation.

In some embodiments, the platelet-mediated FGL2 activity being measured in a contemplated method is thrombin generation.

In some embodiments, platelet-mediated FGL2 units are measured.

Optionally, measuring the FGL2 activity level in the sample at different time points in the course of a treatment of the malignant proliferative disease or disorder, include measuring FGL2 activity level in one or more samples obtained from the diseases subject before application of an anti-malignant therapy or treatment protocol, one or more samples obtained from the subject in the course of anti-malignant therapy, preferably at different time points, and/or one or more samples obtained from the subject after end of treatment protocol, preferably at different time points after treatment completion. Monitoring or following up the outcome of a treatment may be effected, for example, by comparing the platelet-mediated FGL2 activity level in a given time point during the course of a treatment to the activity level measured in antecedent time point and/or to the FGL2 activity level at the beginning of the treatment.

Thus, use of platelet-mediated FGL2 activity level is herein contemplated for the detection and diagnosis of cancer per se, as well as in assessing prognosis of a cancer which has already been diagnosed. Alternatively, FGL2 coagulation activity is also appropriate for cancer screening, since its detection is based on a blood sample, which is one of the most "patient friendly" types of sample to be obtained from subjects.

The terms "coagulation" or "clotting" as used herein refer to the process by which blood changes from a liquid to a gel, forming a blood clot. It potentially results in hemostasis, the cessation of blood loss from a damaged vessel, followed by repair. The mechanism of coagulation involves activation, adhesion, fibrin formation and aggregation of platelets along with deposition and maturation of fibrin. Disorders of coagulation are disease states which can result in bleeding (hemorrhage or bruising) or obstructive clotting (thrombosis).

Coagulation begins almost instantly after an injury to the blood vessel has damaged the endothelium lining the vessel. Leaking of blood through the endothelium initiates two processes: changes in platelets, and the exposure of subendothelial tissue factor (TF) to plasma Factor VII (FVII), which ultimately leads to fibrin formation. Primary hemostasis is attributed to platelets which immediately form a plug at the site of injury.

Platelets are disc shaped, anucleate cellular fragments derived from megakaryocytes. They have a pivotal role in hemostasis by forming the initial hemostatic plug that provides a surface for the assembly of activated coagulation factors leading to the formation of fibrin stabilized platelet aggregates and subsequent clot retraction. Platelets contain more than 30 bioactive proteins, many of which have a fundamental role in hemostasis or tissue healing.

Activation of platelets causes the granules present therein to fuse to its cell membrane (also called degranulation) where the secretory proteins (e.g. PDGF, TGF-β etc.) are transformed to a bioactive state by the addition of histones and carbohydrate side chains. The active proteins are then secreted and bind to transmembrane receptors of target cells, which include mesenchymal stem cells, osteoblasts, fibroblasts, endothelial cells and epidermal cells. These agonists bound transmembrane receptors then activate an intracellular signal protein that causes the expression of a gene sequence that directs cellular proliferation, matrix formation, osteoid production, collagen synthesis etc. thus provoking tissue repair and tissue regeneration. The active secretion of these growth factors by platelets begins within 10 min after activation, with more than 95% of the presynthesized growth factors secreted within 1 hour.

Secondary hemostasis is attributed to a cascade of events leading to the generation of a fibrin clot. It is composed of two initial pathways: extrinsic pathway (also known as tissue factor pathway) and intrinsic pathway (also known as the contact activation pathway), which merge into a common pathway that lead to fibrin formation. The pathways are a series of reactions, in which a zymogen (inactive enzyme precursor) of a serine protease and its glycoprotein co-factor are activated to become active components that then catalyze the next reaction in the cascade (i.e., cleaving downstream proteins), ultimately resulting in cross-linked fibrin. Coagulation factors are generally indicated by Roman numerals, with a lowercase "a" appended to indicate an active form.

Most coagulation factors are serine proteases, except for Factors III (tissue factor), V, VIII and XIII (FIII, FV, FVIII and FXIII, respectively). Factor III, FV and FVIII are glycoproteins, and Factor XIII is a transglutaminase. The tissue factor (TF) and contact activation pathways both activate the "final common pathway" of Factor X, thrombin and fibrin The main role of the tissue factor pathway (extrinsic) is to generate a "thrombin burst", a process by which thrombin, the most important constituent of the coagulation cascade in terms of its feedback activation roles, is released very rapidly. The process includes the following steps: TF forms a complex with activated Factor VII (Factor VIIa or FVIIa). Factor VIIa circulates in a higher amount than any other activated coagulation factor. The TF-FVIIa complex activates Factor IX (FIX) and Factor X (FX): it cleaves the Arg-Ile bond in coagulation FX, leading to its activation (i.e., formation of Factor Xa or FXa). Once activated, FXa interacts with its co-factor FVa in the presence of anionic phospholipid and calcium to form the prothrombinase complex. The latter cleaves prothrombin into thrombin. Prothrombin is also known as clotting Factor II (FII), a vitamin K-dependent proenzyme. Thrombin is the enzyme that is responsible for converting fibrinogen into fibrin, the molecular mesh of the clot.

During this process, thrombin also activates clotting Factors V, VIII, and XI through a positive feedback reaction. The activation of FXI leads to the downstream activation of clotting Factor IX, which then complexes with its co-factor FVIIIa in the presence of anionic phospholipid and calcium to form the intrinsic tenase complex ("Tenase" is a contraction of "ten" and the suffix "-ase" used for enzymes). The latter is responsible for further activation of FX by cleaving the same Arg-Ile bond the TF-FVIIa complex cuts. Thus, coagulation is amplified via the intrinsic pathway. The fibrin clot is stabilized through crosslinking by the transglutaminase XIIIa.

"Fibrinogen", also known as Factor I, is the substrate of thrombin and provides the major meshwork of arterial thrombi. It is an extracellular protein found in significant concentrations in the blood plasmas of all vertebrate animals. Although the principal role of fibrinogen has to do with its polymerization into fibrin clots, the protein also interacts with a number of other extracellular proteins, blood platelets, and a variety of cells. Directly or indirectly, the fibrinogen—fibrin system is involved in hemostasis, inflammation, wound healing, and angiogenesis.

The terms "fibrinogen-like protein 2" or "FGL2", as used herein, refers to a member of the fibrinogen-related protein superfamily, and encompasses two structurally and functionally distinct forms: a soluble form sFGL2, expressed and secreted by regulatory T cells, and a membrane-bound form mFGL2, also referred to herein as "FGL2 prothrombinase", which is a serine protease capable of directly cleaving prothrombin (FII) into thrombin while bypassing the canonical coagulation route. Membrane bound FGL2 is expressed on the surface of macrophages, dendritic cells, endothelial cells, epithelial cells and cancer cells, wherein monocytes and lymphocytes are considered the major source of procoagulant potent mFGL2 in PBC. In the context of embodiments described herein, the terms FGL2 and mFGL2 are used interchangeably and refer to the potent prothrombinase form of FGL2.

Fibrinogen-like protein 2 is capable of directly cleaving prothrombin to thrombin in the absence of factor VII or factor X, leading to fibrin deposition, thus triggering thrombosis.

As shown in the Examples disclosed herein, a correlation has been established between coagulation activity in peripheral blood samples and cell types and counts. Surprisingly, measured FGL2 prothrombinase coagulation activity was directly correlated with the number of platelets in the blood sample. Platelet-free samples were unable to induce coagulation. The occurrence of active FGL2 in platelets may impart platelets with the many functions that are associated with FGL2.

A contemplated method disclosed herein utilized the platelets assay, which effects platelet-mediated FGL2 coagulation activity. The coagulation time (CT) is measured and translated into FGL2 activity level. The extent of FGL2-induced coagulation level, in turn, provides a means to assess the existence of a malignant process in a subject, and/or to monitor anti-malignant treatment efficacy in a subject inflicted with a malignant disease.

The term "platelet-mediated FGL2 coagulation activity" as used herein, refers to a coagulation process, as defined herein, namely, the formation of a clot, which is, at least partially, effected by FGL2 associated with platelets.

A first step in a contemplated method is obtaining a biological sample from the subject, essentially containing platelets derived from the subject.

As defined herein, "biological sample" refers to any sample obtained from a subject, generally a mammalian subject, more specifically a human subject. Examples of biological samples include body fluids and tissue specimens. The source of the sample may be blood, cerebrospinal fluid, tissue scrapings, swabs taken from body regions (throat, vagina, ear, eye, skin, sores tissue, such as lymph nodes, or the like). Tissue specimens include tumor biopsies or biopsies from any organ, such as spleen, lymph nodes, liver, lung, mammary gland, pancreas, colon, uterus, skin, prostate, endocrine glands, esophagus, stomach, intestine, etc. In particular, a sample may be obtained from any lymphocyte-containing tissue.

In some embodiments, the sample is a blood sample, such as, but not limited to, a whole blood sample. Usually, the plasma is removed from the blood sample.

In some embodiments, the sample comprises peripheral blood mononuclear cells (PBMC). In accordance with these embodiments, the PBMC sample is further supplemented with platelets, optionally admixed therewith. The platelets may be extracted form the same blood sample of from another blood sample obtained from the same subject. Alternatively, the PBMC sample may comprise platelets derived form a different subject, for example a subject suspected of having a malignant disease, provided that the PBMC sample is free of its original platelets.

A peripheral blood mononuclear cell is defined as any blood cell with a round nucleus. These cells consist of lymphocytes and monocytes, whereas erythrocytes and platelets have no nuclei, and granulocytes (neutrophils, basophils, and eosinophils) have multi-lobed nuclei. The lymphocyte population consists of T cells, B cells and Natural Killer cells. These blood cells are a critical component in the immune system to fight infection and adapt to intruders.

Techniques for extraction, isolation and/or separation of PBMC from whole blood are known in the art and thoroughly explained in the literature. For example, PBMC—most specifically lymphocytes and monocytes cells—can be separated from whole blood using a method known as Ficoll or polysucrose-sodium metrizoate medium (Ficoll-Paque™). Ficoll is a hydrophilic polysaccharide, and ficoll medium forms a density gradient that separates layers of blood, as different components of the blood have different densities and can be separated accordingly. This density gradient medium has a density of 1.08 g/ml, and is denser than lymphocytes, monocytes, and platelets (meaning these will remain above it), but less dense than granulocytes and erythrocytes, which will drop below it during the centrifugation stage of the procedure. The peripheral blood is supplemented with anticoagulant (e.g., heparin, EDTA, citrate, ACD-A or citrate phosphate dextrose (CPD) and diluted with PBS prior to gently layering it over an equal volume of Ficoll in a sterile centrifuge tube (e.g., Falcon tube) and centrifuging for 10-40 minutes, at 300-600 g, depending on the centrifuge apparatus used, optionally without brake. Usually, four layers will form, each containing different cell types: the uppermost layer will contain plasma, which can be removed by pipetting. The second layer will contain PBMC and is a characteristically white and cloudy "blanket." These cells can be gently removed using a Pasteur pipette and added to warm medium or a salt solution (e.g., PBS) to wash off any remaining platelets, Ficoll, and plasma, then centrifuged again. The pelleted cells can then be counted, and the percentage viability estimated using, e.g., Trypan blue staining. Cells can be used immediately or frozen for long-term storage.

Due to the extreme care that must be exercised when pipetting blood on to the separation medium, alternative methods have been devised. In one such procedure a sample of the diluted blood is placed in a centrifuge tube and Ficoll-Paque (or equivalent separation medium with a density of 1.077) is added by being underlayered under the blood. This method creates cleaner interfaces than those obtained when blood is layered over the Ficoll, since there is less disturbance of the surface of the Ficoll and less mixing.

Alternative gradient centrifugation employing specially designed centrifugation tubes and gradient solutions or gels such as currently known in art or to be developed in the future are also suitable for the purpose of a contemplated diagnosis and/or prognosis method. Non-limiting examples include UNI-SEP tubes (Novamed, Jerusalem, Israel), BD Vacutainer® cell preparation tube (CPT™) (BD, Franklin Lakes, NJ, USA), Leucosep® tube (Greiner Bio-One, Kremsmuenster, Austria), Accuspin™ tubes (Sigma Chemical Co), SepMate™ (Stemcell™, Petach Tiqua, Israel) techniques.

PBMC isolation by CPT™, SepMate™ and UNI-SEP tubes is straightforward and requires limited sample handling compared to Ficoll isolation and, furthermore, results in a higher recovery than Ficoll isolation.

In an exemplary embodiment, PBMC are separated using UNI-SEP tubes.

In some embodiments, the biological sample is a platelet-rich plasma (PRP).

"Platelet-rich plasma" or "PRP" is plasma with many more platelets than what is typically found in blood, namely, a concentrate of platelet-rich plasma protein derived from whole blood, centrifuged to remove red blood cells. As a concentrated source of blood plasma and autologous conditioned plasma, PRP contains several different growth factors and other cytokines that can stimulate healing of soft tissue and joints. It has a greater concentration of growth factors than whole blood (5 to 10 times greater or richer than usual), and has been used to encourage a brisk healing response across several specialties, in particular dentistry, orthopedics and dermatology.

To obtain a PRP preparation, blood is first drawn from a patient. A 30 ml venous blood draw will yield 3-5 ml of PRP depending on the baseline platelet count of an individual, the device used, and the technique employed. The blood draw occurs with the addition of an anticoagulant, such as citrate dextrose A to prevent platelet activation prior to its use.

The PRP preparation is based on difference of specific gravity of blood cells, and employs a differential centrifugation, whereby an initial centrifugation to separate red blood cells (RBC) is followed by a second centrifugation to concentrate the platelets, which are suspended in the smallest final plasma volume. After the first spin step, the whole blood separates into three layers: an upper layer that contains mostly platelets and WBC, an intermediate thin layer that is known as the buffy coat and that is rich in WBCs, and a bottom layer that consists mostly of RBCs. For the production of pure PRP (P-PRP), upper layer and superficial buffy coat are transferred to an empty sterile tube. For the production of leucocyte rich PRP (L-PRP), the entire layer of buffy coat and few RBCs are transferred along with the platelets layer. The second spin step is then performed. 'g' for second spin should be just adequate to aid in formation of soft pellets (erythrocyte-platelet) at the bottom of the tube. The upper portion of the volume that is composed mostly of platelet-poor plasma (PPP) is removed. Pellets are homogenized in lower ⅓rd (5 ml of plasma) to create the PRP.

In some embodiments, a PRP sample does not contain white blood cells. Such a sample is also referred to as pure platelet-rich plasma (P-PRP) or leucocyte-poor PRP sample.

In some embodiments, the biological sample comprises pure platelets.

In accordance with a contemplated method, the platelets in a platelet-containing biological sample are initially carefully counted and their number is recorded. Platelet count is done before sample preparation for analysis, and optionally, the WBCs are counted as well.

The platelets count in a platelet-containing biological sample as defined herein, for example PRP, PBMC or a whole blood sample, is in the range of from about $15 \times 10^6$ to about $500 \times 10^6$ platelets per sample. For example, a PRP sample may comprise from about $15 \times 10^6$ to about $30 \times 10^6$ platelets, from about $25 \times 10^6$ to about $50 \times 10^6$ platelets, from about $50 \times 10^6$ to about $80 \times 10^6$ platelets, from about $80 \times 10^6$ to about $110 \times 10^6$ platelets, from about $100 \times 10^6$ to about $150 \times 10^6$ platelets, from about $150 \times 10^6$ to about $250 \times 10^6$ platelets, from about $250 \times 10^6$ to about $300 \times 10^6$ platelets, from about $250 \times 10^6$ to about $300 \times 10^6$ platelets, from about $280 \times 10^6$ to about $350 \times 10^6$ platelets, from about $350 \times 10^6$ to about $400 \times 10^6$ platelets, or from about $400 \times 10^6$ to about $500 \times 10^6$ platelets per sample, and any intermediate count therebetween.

In principle any count of platelets can be measured rather accurately using auto cell counter facilities. However, practically, reliable activity can be measured for at least $\sim 20 \times 10^6$ platelets per sample. A count of 100 million platelets per sample provide a balance between significant activity and obtainable platelets counts from normal sample size ($\sim 2$-10 ml). Moreover, above certain number of platelets in the sample the activity often does not increase ($\sim 500 \times 10^6$ platelets).

In some exemplary embodiments, a platelet-containing sample comprises about $25\times10^6$ platelets, about $50\times10^6$ platelets, about $75\times10^6$ platelets, about $100\times10^6$ platelets, about $125\times10^6$ platelets, about $150\times10^6$ platelets, or about $200\times10^6$ platelets.

Platelets concentration in a prepared PRP sample is in the range of form about $100\times10^6$ platelets/ml to $1000\times10^6$ platelets/ml. For example, form about $100\times10^6$ platelets/ml to $200\times10^6$ platelets/ml, form about $150\times10^6$ platelets/ml to $250\times10^6$ platelets/ml, form about $250\times10^6$ platelets/ml to $350\times10^6$ platelets/ml, form about $300\times10^6$ platelets/ml to $400\times10^6$ platelets/ml, form about $350\times10^6$ platelets/ml to $450\times10^6$ platelets/ml, form about $400\times10^6$ platelets/ml to $500\times10^6$ platelets/ml, form about $500\times10^6$ platelets/ml to $600\times10^6$ platelets/ml, form about $600\times10^6$ platelets/ml to $700\times10^6$ platelets/ml, form about $700\times10^6$ platelets/ml to $900\times10^6$ platelets/ml or form about $800\times10^6$ platelets/ml to $1000\times10^6$ platelets/ml, and any intermediate ranges therebetween.

In some exemplary embodiments, a platelet-containing sample comprises about $300\times10^6$ platelets per ml, about $400\times10^6$ platelets per ml, about $500\times10^6$ platelets per ml or about $600\times10^6$ platelets per ml.

In some embodiments, a pre-determined, fixed number of platelets or platelets concentration is employed in a contemplated method described herein. Since activity of FGL2 is dependent on platelets count, it is crucial to use constant, pre-determined count or concentration of platelets in each sample being diagnosed so as to obtain consistency and comparability both with reference to control levels as well as with reference to subsequent PRP, PBMC and/or whole blood samples taken from the same subject either simultaneously or at different time points, such as when monitoring a course of treatment protocol.

Additionally or alternatively, the platelets number can be normalized or standardized. Normalizing the platelet number can be performed, for example, by adjusting the sample size to include a constant number of platelets, or by mathematically manipulating e.g., the resultant coagulation time according to the platelet count. When using a constant count (or concentration) of platelets in a sample is not feasible, FGL2 activity levels or coagulation time measured in a given sample may be normalized such that it would correspond to the FGL2 activity level measured in a sample comprising a known, predetermined platelets count. This may be accomplished by generating a calibration curve using a range of platelets count in the sample versus the resulting coagulation time. In addition, the FGL2 activity level may be normalized to the baseline platelet count of an individual.

The second step in a contemplated diagnosis or treatment monitoring method described herein is promoting FGL2-induced coagulation process in the biological sample.

There are several ways to evoke FGL2 activity in the test sample. For example, in a plasma-free test sample (biological sample) such as PMBC sample, prothrombinase activity by FGL2 may be induced by addition of FGL2 prothrombinase substrate such as prothrombin (Factor II), a derivative or an analog thereof, a non-thrombin synthetic chromogenic substrate or any combination thereof, preferably containing FGL2 cleavage site. Non-limiting examples of a prothrombin derivative or analog include a functional segment of the wild type prothrombin, or prothrombin comprising chromogenic or fluorescent moieties.

In a PRP sample, FGL2 coagulation activity may be induced by the addition of FXDP and tissue factor (TF) or an artificial TF surrogate. Accordingly, sample aliquots comprising predetermined amounts of platelets may be centrifuged to obtain dry pellets which are then suspended in a predetermined amount of FXDP, e.g., 200 ill FXDP.

"Factor X deficient plasma", as referred to herein, is a lyophilized stable human plasma with a coagulation activity <1% of Factor X. All other coagulation factors are in the normal range, including Factor II (prothrombin) and fibrinogen (Factor I). Factor X deficient plasma is manufactured from pooled normal human plasma depleted of FX using antibodies directed to FX. Factor X deficient plasma is generally used for the determination of FX: when a patient's plasma is mixed with FXDP, the degree of correction of thrombin (or coagulation) is proportional to the level of factor X in the patient's plasma. Factor X deficient plasma is commercially available, for example, STA-deficient X, manufactured by Stago (catalog number: 00738), Technoclone Factor X Deficient Plasma manufactured by Diapharma® ((catalog number: 5174006), or VisuDep-F Frozen Factor X Deficient Plasma manufactured by Affinity Biologicals™.

Tissue factor is added to a PRP sample in order to activate the extrinsic pathway of clot formation, which will initiate thrombin generation that will ultimately activate, in a positive feedback reaction, the FGL2-mediated pathway and merge therewith in converting prothrombin to thrombin, resulting in formation of fibrin clot. In some exemplary embodiments, a recombinant human TF is used. Usually a commercially available recombinant human or rabbit TF is utilized.

Optionally, before measurement of FGL2 activity, the sample undergoes cell-lysis and homogenization. Several methods may optionally be used to physically lyse the cells in the biological sample tested, including mechanical disruption, liquid homogenization, high frequency sound waves (sonication), freeze/thaw cycles, chemical reagents-based lysis and manual grinding. In some exemplary embodiments, sample lysis is conducted by sonication.

Optionally, coagulation activity in induced and conducted at 37° C.

The third step in a contemplated method described herein is measuring the platelet-mediated FGL2 activity level in the sample.

In some embodiments, platelet-mediated FGL2 activity level in assessed by measuring the fibrin clot generation time.

As used herein, the term "fibrin clot generation time" is interchangeable with the terms "coagulation time (CT)", "clotting time", "coagulation activity", and "fibrin generation", all of which refer to the time that laps from time point zero in which all conditions and reagents for forming clot are provided to the sample, until fibrin clot becomes detectable in the sample, namely until a critical mass of fibrin has been formed such that it can effect measurable physical properties of the sample such as light absorbance, viscosity, electric current conductance and the like.

Coagulation time in a sample obtained from "healthy subject" or "normal subject", both terms herein denoting a subject not inflicted with a malignant disease, are likely to range between 80 and 400 seconds. However, shorter and longer times are possible, depending on the platelets count in the sample and FGL2 activity.

Shortening of CT, in accordance with embodiments described herein, is indicative of the existence of a malignant disease or disorder in the subject. Thus, a malignant disease may be diagnosed in subject if the CT as measured in a platelet-containing sample obtained from the subject is in the range of, for example, from about 20 second to about 300 seconds, for example, about 20 sec, about 30 sec, about 40 sec, about 50 sec, about 60 sec, about 70 sec, about 80 sec, about 90 sec, about 100 sec, about 120 sec, or about 200 sec.

In some embodiments, platelet-mediated FGL2 activity level in assessed by measuring FGL2-induced thrombin generation (TG).

Optionally, TG or CT is measured, for example, by monitoring changes in light absorption, viscosity and/or electrical current in a test sample in the course of thrombin formation or fibrin clot formation, respectively.

In some embodiments, automatic or semi-automated data generation and/or measurement is employed. Use of automated devices affords rapid collection and recordation of sample data, and minimizes inaccuracies often encountered in manual measurements of coagulation time and/or thrombin generation.

In exemplary embodiments, a coagulation analyzer or a coagulometer is employed, utilizing photospectroscopy for monitoring coagulation, such that changes in light absorbance by the test sample as a result of clot formation are monitored and recorded. Optionally, a coagulometer automatically tests small amounts of sample, for example, 50 µl and automatically adds TF and/or other activators and co-factors required for coagulation such as, but not limited to, calcium ions and phospholipids. A non-limiting example of such coagulometer is ACL TOP® 500 (Instrumentation Laboratory (IL)).

In embodiments featuring spectroscopically, measurement of CT or thrombin generation time is determined by the inflection point in the absorption versus time curve (i.e., first derivative peak).

In order to standardize or normalize the coagulation time measured in a sample, CTs are converted to FGL2 activity level using a calibration curve. Normalization is necessary in order to exclude inaccuracies in FGL2 activity resulting from, e.g., inconsistency between manufacturers, lots, reagents and/or inaccuracies in measurements inherent to the devise being used. Thus, the FGL2 activity level in a sample is calculated based on a set of standard samples of known FGL2 concentrations.

The term "calibration curve" as used herein refers to a plot of how the instrumental response, the so-called analytical signal, changes with the concentration of the analyte (the substance to be measured). A series of standards across a range of concentrations near the expected concentration of analyte is first prepared (the concentrations of the standards must lie within the working range of the technique (instrumentation) being used). Analyzing each of these standards using the chosen technique will produce a series of measurements. For most analyses a plot of instrument response vs. concentration will show a linear relationship. The measured response of the analyte can then be interpolated to find the unknown concentration of analyte using the calibration curve.

Translation of clotting time into coagulation activity level can be made, for example, by conversion of the clotting time to Factor X activity percentages using a predetermined calibration curve of FX. To generate such a calibration curve, serial dilutions of calibrated normal human plasma are generated by mixing the normal plasma with FXDP, optionally automatically e.g., by a coagulometer. The Factor X concentrations in the calibration standards for the calibration curve may correspond to a range of FGL2 activity of from about 0.5% to about 100% activity. Coagulation time is measured for each FX concentration.

Alternatively, any other prothrombinase may be used for the preparation of a calibration cure, for example purified natural or recombinant FGL2.

Optionally, calibration curves are also conducted automatically. Therefore, both the pipetting and the temperature control are monitored and accurate, contributing to the overall reliability of the analysis.

In some embodiments, FGL2 activity level is assessed by measuring thrombin generation. In some exemplary embodiments, measuring of the thrombin generation time is performed using an extended prothrombin time (PT) test. As mentioned herein, prothrombinase activity is understood to be FGL2 prothrombinase activity, since the test biological sample (e.g., PRP or PMBCs) contains only FGL2 and no other prothrombinase. Therefore, addition of prothrombin (specific substrate) to the lysates of these cells containing FGL2 is expected to generate thrombin (specific end product). The thrombin generation assay, is described, for example, in U.S. Pat. No. 9,023,609, in Ghanekar et al. (Ghanekar et al., *J. Immunol.*, 172:5693-701, 2004), and in the Examples section herein. Essentially, a sample is placed in contact or mixed with prothrombin (obtained from a commercial source) in assay conditions suitable for FGL2 prothrombinase activity. Thrombin generation may be detected through the cleavage of its chromogenic substrate (for example, S-2238™, formula: H-D-Phe-Pip-Arg-pNA.2HCl), which results in change of color, meaning that enzymatic activity of the generated thrombin is detected and measured through its end product. Coagulation activity in a test sample may optionally be calculated based on a comparison with the standard curve generated by known concentrations of thrombin.

Other methods for detecting thrombin could be envisioned, including immunological methods, which could measure the amount of thrombin generated directly, using e.g., anti-thrombin antibodies.

The fourth step in a contemplated method described herein is comparing the measured platelet-mediated FGL2 activity level with that of a control value. Platelet-mediated FGL2 coagulation activity level or platelet-mediated thrombin generation level higher than control may indicate the presence of a malignant proliferative disease or disorder.

As referred to herein, the term "control" or "control sample" refer to a sample or pool of samples obtained from subjects not affected by proliferative malignant disorder, otherwise referred to as the "normal population". Similarly, "control value" relates to the level of FGL2 activity level, for example fibrin generation or thrombin generation levels, presented by a control sample. The "control value" may also refer to the mean value of FGL2 activity level obtained from studies in the normal population. The control sample or control value is the source of reference with which to compare the sample that diagnose is sought after.

The control level may be a FGL2 activity level measured in a biological sample (e.g., PRP, PMBCs, tissue biopsy) taken from a healthy or normal subject as defined herein. Such sample is also referred to herein as "normal sample". Normal samples may be used as a control when a contemplated diagnosis method is used for a first diagnosis of a malignant disease in a subject suspected of having been inflected with a malignant disease. The normal sample may an autologous sample taken for the same subject when known to be a healthy subject as defined herein. Additionally or alternatively, when first diagnosis is pursued, the normal sample may be obtained from another healthy subject.

In general, finding elevated FGL2 enzyme activity when compared with that of a control value indicates the presence of a malignant disorder. In counterpart, a sample presenting a FGL2 enzyme activity which is compatible, i.e., within, the range or lower than that of a control value, indicates the absence of a malignant disorder.

A "normal" FGL2 activity level, namely FGL2 activity level in a sample obtained from a healthy subject relies on data base achieved from a large number of FGL2 activity tests of healthy subjects.

When a contemplated diagnosis method is employed in monitoring the efficacy of anti-cancer treatment in a subject, the control may be a sample obtained from the subject before the anti-cancer treatment commenced. In this case, FGL2 activity level in the untreated subject serves as a baseline, and FGL2 activity levels measured at least once during treatment and at least once after completion of treatment may be used to for assessing prognosis of the anti-cancer treatment.

Prognosis of a malignant, disorder may be effected by measuring FGL2 activity level in a sample obtained on at least one time point throughout treatment. If a sample is obtained at only one time point, this time point, should be after treatment. An optimal procedure would involve measuring FGL2 activity level at least once before, during and after treatment of a malignant disease. When the pattern of FGL2 activity level of a subject is the closest to that of the normal population, it indicates a successful treatment. Thus, a decrease of FGL2 activity throughout time as compared to the baseline activity is being indicative of recovery or amelioration of the malignant condition.

On the other hand, a high or increasing level of FGL2 activity level as comparable to a normal sample, or to the subject's baseline FGL2 activity level and/or to an antecedent measured level (for example, a time point just prior to a given time point), or even higher, may be indicative of no response to treatment or of poor prognosis, treatment failure, and/or relapse, depending on each case. Poor prognosis meaning that there is a worsening of the malignant disorder, which may, e.g. be demonstrated by the enlargement of a tumor, in case of solid tumors, or in an increase of circulating cancer cells, in case of leukemias.

"Therapy of a malignant proliferative disease or disorder", as referred to herein, relates to any treatment for eradicating a malignant, proliferative disease, such as, but not limited to, radiotherapy, chemotherapy, immunotherapy, surgery, biologic therapy, targeted therapy, stem cells transplant, hyperthermia, photodynamic therapy, blood transfusion and donation, laser treatment, complementary and alternative therapy and any combination thereof, as well known in the art.

As used herein, terms such as "tumor", "cancer", "malignant", "proliferative disorder" and "malignancy" all relate equivalently to an uncontrolled hyperplasia of a tissue or organ. If the tissue is part of the lymphatic or immune systems, malignant cells may include, non-solid tumors of circulating cells (e.g., hemalogical malignencies). Malignancies of other tissues or organs may produce solid tumors. When referring herein to the term malignant proliferative disease or disorder, or cancer, it includes solid and non-solid tumors.

More particularly, solid tumors include carcinomas, sarcomas, melanomas and adenomas. Some specific and non-limiting examples of cancer are pancreatic cancer, breast cancer, squamous cell carcinoma, multiple myeloma, prostate cancer, Langerhans cell sarcoma, thyroid papillary cancer, esophageal cancer, endometrial sarcoma, mammary gland cancer, mediastinal large cell lymphoma, Hodgkin lymphoma, lung carcinoma, small cell lung cancer or non-small-cell lung carcinoma, kidney, uterus, prostate, bladder, colon, or ovarian cancer.

Other solid tumors which may also be diagnosed and/or monitored by a contemplated method described herein are, for example, mixed tumors of salivary gland, tumors in lip and oral cavity, carcinoma of the eyelid and carcinoma of the conjunctiva, pharynx, larynx, paranasal sinuses, colonic adenomas, adenocarcinomas sarcomas, liposarcoma, myxoid, synovial sarcoma, rhabdomyosarcoma (alveolar), extraskeletal myxoid chondrosarcoma, Ewing's tumor, testicular and ovarian dysgerminoma, Wilms' tumor, neuroblastoma, skin malignant melanoma, mesothelioma, melanoma of the conjunctiva, malignant melanoma of the uvea, retinoblastoma carcinoma of the lacrimal gland, sarcoma of the orbit, brain cancer, spinal cord cancer, vascular system cancer, hemangiosarcoma, malignant lymphoma, such as Burkitt's or non-Hodgkin's and Kaposi's sarcoma.

Non-solid tumors that may be diagnosed, prognosed, followed up and/or monitored by a contemplated method described herein include, but are not limited to, mycosis fungoides, Sézary syndrome, myeloid leukemia such as chronic myelogenous leukemia, acute myelogenous leukemia, acute myelogenous leukemia with maturation, acute promyelocytic leukemia, acute non-lymphocytic leukemia, acute non-lymphocytic leukemia with increased basophiles, acute monocytic leukemia, acute myelomonocytic leukemia with eosinophilia, lymphocytic leukemia such as acute lymphoblastic leukemia, chronic lymphocytic leukemia and myelo-probferative diseases.

The methods described herein for detection, diagnosis, follow-up and/or assessment of prognosis, are suitable for any stage in cancer.

In some exemplary embodiments, a contemplated method for determining platelet-mediated FGL2 activity level is applied for diagnosis of mycosis fungoides (MF) and the Sézary syndrome. These are diseases in which lymphocytes become malignant and affect the skin. Cancer cells of mycosis fungoides and the Sézary syndrome are able to spread from the skin to other parts of the body (either through tissue, the lymph system, or the blood). Recurrent MF and the Sézary syndrome may come back in the skin or in other parts of the body.

Despite being the two most common types of cutaneous T-cell lymphoma, the diagnosis of MF or the Sézary syndrome is entirely based on the pathologic workup of patients with suspicious clinical presentation. No molecular biomarkers are currently available.

A contemplated method for diagnosis, monitoring, follow-up and/or prognosis as described herein may particularly be useful when accompanying any common diagnostic tests, such as, but not limited to, physical examination; other laboratory tests (blood, urine, and the like); biopsy; imaging tests such as PET, computed tomography (CT), magnetic resonance imaging (MRI), X-ray, ultrasound, and the like; nuclear medicine scans (e.g., bone scans); endoscopy; and or genetic tests.

For example, it is shown herein in Example 8, that platelet-assay described herein conducted in aggressive lymphoma patients during a treatment protocol was well correlated with PET scans performed to these patients at several time points during treatment. Hence, while PET often cannot not be performed for a period of several months (2-7 months) during treatment, in order to minimized exposure of the patients to hazardous radiation, as well as due to over-loads in the facilities and costs considerations, platelet-mediated FGL2 activity level assay could be performed as often as desired in order to obtain a tight follow up of therapy efficacy. Often, a contemplated platelet-assay can diagnose relapse well before it is observed by e.g., PET, CT or MRI, and provide valuable information about the effectivity of the treatment protocol.

An aspect of the disclosure is related to a kit for diagnosis, follow-up or prognosis of a malignant disease or disorder, the kit comprising: (a) at least one reagent for measuring platelet-mediated FGL2 activity level as defined herein; (b) instructions for measuring FGL2 activity level in a sample; and, optionally, (c) at least one means for collecting a sample to be tested; and/or (d) at least one control sample.

Reagent for measuring platelet-mediated FGL2 activity level may include reagents relevant to the platelet-mediated FRGL2 activity test used. When a kit designed to assess thrombin generation level is contemplated, it may contain an FGL2 substrate such as prothrombin, an active segment thereof, a derivative thereof, a homolog thereof, or any chromogenic substrate suitable for the determination of serine proteases.

When a kit designed to assess FGL2 coagulation activity level is contemplated, it may contain FXDP, calcium and optionally phospholipids.

Further reagents include, for example, buffers such as HEPES, PBS, Tris, or any other buffer suitable known in the art, and any other necessary reagent known to the man skilled in the art.

A non-limiting list of means for collecting a sample to be tested includes syringes, needles, in particular blood collection needles, sample tubes, and any other device necessary for collecting a sample as known to the man skilled in the art.

The kit may further optionally comprise any other necessary reagents such as detectable moieties, enzyme substrates and color reagents. The particular reagents and other components included in the contemplated diagnostic kit can be selected from those available, in the art in accord with the specific diagnostic method practiced in the kit. Such kit can be used to detect FGL2 activity level in biological samples, such as tissue samples, particularly whole blood, bone-marrow, PRP, PBMC or other cells before and/or after culture, obtained from a subject, as long as the sample contains platelets.

As used herein the term "about" refers to ±10%

The terms "comprises", "comprising", "includes", "including", "having" and their conjugates mean "including but not limited to".

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839, 153; 3,850,752; 3,850,578; 3,853,987; 3,867,517; 3,879, 262; 3,901,654; 3,935,074; 3,984,533; 3,996,345; 4,034, 074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Other general references are provided throughout this document. The procedures therein are believed to be well known in the art and are provided for the convenience of the reader. All the information contained therein is incorporated herein by reference.

Materials and Methods (i) Study Population

Peripheral blood samples were collected from 142 subjects. The population included healthy volunteers (n=65) and hospitalized patients (n=77) admitted to an internal medicine department with clinical diagnosis of a bacterial infection (n=47) or viral infection (n=30). Patients were enrolled during their first hospitalization day. Patients diagnosed with malignant diseases or any other proliferative diseases backgrounds were excluded.

Malignant disease state follow-up was performed in individual patients diagnosed with cancer, by monitoring FGL2 activity in platelet samples of patients with aggressive lymphoma (26 patients), every three months. The activity was determined also in approximate to disease state diagnosis by PET scan.

The study was approved by the hospital's Institutional Review Board. Informed consent was obtained from all participants.

(ii) Cell Cultures

Prostate cancer PC-3 cell line established from human prostate carcinoma was cultured in F12 with 10% fetal calf serum and 1% penicillin and streptomycin. A human leukaemic cell line CMK, established from human acute megakaryocytic leukemia was cultured in RPMI 1640 with 20% fetal calf serum and 1% penicillin and streptomycin.

(iii) FGL2 Cloning and Overexpression in PC-3 Cells

The complete cDNA sequence of human FGL2 (encoding for 439 aa protein) was inserted into pCDNA3.1 vector (Invitrogen) under CMV promoter to provide constitutive overexpression. The construct was assembled using a restriction-free cloning technique. Fibrinogen-like protein 2 fragment was amplified (using primers 5'-CTGTACGAC-GATGACGATAAGAAGCTGGCTAACTGGTACTGGC-3' and 5'-CCACACTGGATCCTAGGTACTTATGGCT-TAAAGTGCTTGGGTCTG-3') and the vector fragment was amplified (using primers 5'-GTACCTAG-GATCCAGTGTGG-3' and 5'-CTTATCGTCATCGTCGTA-CAG-3'). Both reactions were treated with DpnI restriction enzyme (New England Biolabs). The FGL2 and vector fragments were then allowed to anneal by slow temperature cool down. Annealed fragments were ligated and amplified by PCR. All DNA amplification reactions were conducted using PFU Ultra II high fidelity DNA polymerase (Agilent). Vectors carrying complete FGL2 were isolated and transfected into PC-3 using Dharmafect-4 reagent according to manufacturer instructions. Stable clones harboring the FGL2 insert were obtained using neomycin (250 µg/ml G-418) as a selective marker. Fibrinogen-like protein 2 overexpression was verified by real-time PCR and western blotting at the transcription and translation levels, respectively.

(iv) Peripheral Blood Cell Isolation

Whole blood samples were collected in EDTA tubes. The peripheral blood cells (PBC; white blood cells and platelets) were isolated by layering onto polysucrose and sodium metrizoate solution in sterile plastic centrifuge UNI-SEP tubes (Novamed). UNI-SEP tubes contain a solution of 5.6% polysucrose and 9.5% sodium metrizoate, sequestered in the bottom of the tubes by one-way plastic inserts. Blood poured into the insert does not disrupt the surface of the polysucrose-sodium metrizoate layer. During centrifugation, the insert opened to permit mixing of the blood and polysucrose-sodium metrizoate. Aggregated red blood cells and granulocytes sedimented to the bottom of the tube while the white blood cells migrated to the interface between the plasma and polysucrose-sodium metrizoate layers. They were readily identified as a discrete white band located above the plastic insert.

Following centrifugation (750×g, 30 min, 20° C.), the entire content of the tube above the UNI-SEP insert was collected and washed 3 times (4500×g, 7 min, 20° C.) using PBS (calcium and magnesium free). When sample preparation required minimal presence of platelets, the mononuclear layer was removed from the UNI-SEP tubes and washed 3 times with PBS (500×g, 10 min, 20° C.). The sample was counted using ADVIA® 2120i CBC automatic analyzer (Siemens) to determine the precise cell content.

(v) Platelet Isolation

Ten milliliters of whole blood samples were collected into tubes containing EDTA. Platelet-rich plasma (PRP) was obtained by centrifugation (200×g, 20 min, 20° C.). The top fraction containing the plasma (0.5 ml) was removed and centrifuged (4500×g, 5 min, 20° C.). The plasma was removed and the pellet was washed twice with 15 ml PBS (4500×g, 5 min, 20° C.). The washed pellet was suspended in 1 ml PBS. Absence of white blood cells was confirmed by a sensitive automatic cell counter (XN-1000 R™ Hematology Analyzer, Sysmex). In cases the prevention of platelets activation was desired, CTAD solution (11 mM citric acid, 1.5 mM theophylline, 0.02 mM dipyridamole and 0.37 mM adenosine) was added to the sample in all steps.

(vi) Thrombin Generation Assay

Activity assay was performed as previously described (Rabizadeh et al. PLoS One, 9:e109648, 2014). Thrombin generation analysis was based on Ghanekar et al. (Ghanekar et al., J. Immunol., 172:5693-701, 2004) with modifications. Predetermined amounts of cells were aliquoted, homogenized, mixed with human prothrombin (Stago, 10 mM final concentration) and incubated for 30 min at 37° C. to allow the generation of thrombin. The reaction was terminated and the amount of generated thrombin was measured using a chromogenic substrate (S-2238™, formula: H-D-Phe-Pip-Arg-pNA.2HCl, molecular weight: 625.6; Chromogenix) and calculated according to a standard curve comprised of human thrombin with known international unit (IU) concentrations (Omrix).

(vii) Semi-Automated Assay for Prothrombinase-Induced Coagulation Activity

Prothrombinase activity present in peripheral blood samples was measured by an automated coagulation analyzer (ACL TOP® 500, IL), based on extended prothrombin time (PT) coagulation test. Platelet-rich plasma (PRP) was prepared from peripheral blood samples (700×g, 10 min, 20° C.). The PRP fraction was centrifuged (4500×g, 7 min, 20° C.) and the supernatant was discarded. The pellet was washed twice using 15 ml PBS, resuspended in 4 ml PBS and counted (ADVIA® 2120i, Siemens) to determine the precise cell content. Predetermined amounts of cells were aliquoted, centrifuged (7500×g, 5 min, 20° C.) and the dry pellet was stored in −80° C. until analysis.

To determine the coagulation activity, the cell pellet was suspended in 200 µl factor X deficient plasma (FXDP, Stago), homogenized for at least 1 minute by sonication and analyzed for fibrin clot formation using automated coagulation analyzer: fifty microliters of sample were mixed with 100 µl of recombinant human tissue factor (Recomboplastin, IL). Clotting time was determined by the inflection point in the coagulation curve (i.e., first derivative peak). Coagulation time ranged between 90 and 400 seconds.

In transforming clotting time into prothrombinase activity values, FGL2 activity levels are expressed herein, for convenience, in FX prothrombinase activity values (expressed in percentages). Conversion of clotting time into prothrombinase activity was made using a predetermined calibration curve of factor X. To generate the calibration curve, serial dilutions of calibrated normal human plasma (Instrumentation Laboratory, USA) were automatically generated using the ACL-TOP® 500 (Instrumentation Laboratory) instrument by mixing with FXDP (Stago) at various ratios. Factor X activities ranged from 50% to 0.5% activity. Prothrombin time coagulation test was performed for each concentration of factor X in triplicates.

In order to determine FGL2 activity in a sample, and be able to compare between samples from different individuals or in different times, the sample should include a constant predetermined number of platelets. Otherwise, the measured activity should be mathematically adjusted according to the number of platelets in the sample. The number of PBMC in the sample is of negligible importance. For convenience, a predetermined count of 100×10^6 platelets per sample was adjusted.

(viii) Immunoprecipitation

Isolated samples were washed and lysed by sonication. Equal aliquots containing 1.5×10^6 WBC or 20×10^6 platelets were incubated with 1 µg of either of the following antibodies for 1 h at 4° C.: monoclonal IgG$_{2a}$ mouse anti-FGL2 (4H5, Santa Cruz); monoclonal rabbit anti-factor-X IgG$_1$ (AHX-5050, Santa Cruz); mouse IgG$_{2a}$ (Santa Cruz); and mouse IgG$_1$ (Santa Cruz). The lysed cell suspension was incubated with protein A/G-agarose beads (Santa Cruz) for another hour at 4° C. The beads were washed four times with PBS supplemented with 0.1% Tween®-20, resuspended in sample buffer containing 2% SDS and 30 mM 3-mercaptoethanol, and boiled for 3 min. Proteins were resolved in 10% polyacrylamide gels and analyzed by western blotting.

(ix) Membrane and Soluble Protein Extraction

Total membrane proteins were separated from the soluble fraction and extracted using the plasma-membrane protein extraction kit (BioVision Incorporated) according to manufacturer directions. All cells were washed with PBS to remove serum proteins prior to cell extraction.

(x) Western Blotting

Proteins were separated by SDS-PAGE (10% acrylamide gels) under reducing conditions and blotted onto a nitrocellulose membrane. The human proteins FGL2, FX and actin were detected using the following primary antibodies: polyclonal rabbit anti-FGL2 IgG (Proteintech); monoclonal mouse anti-FGL2 IgG$_{2a}$ (4H5); monoclonal mouse anti-factor-X IgG$_1$ (AHX-5050); monoclonal mouse anti-β-actin IgG$_1$ (C4) (Santa Cruz). The following fluorophore-linked secondary antibodies were used: IRDye® 680RD goat anti-mouse and IRDye® 800CW goat anti-rabbit (LI-COR). Immunoblots were imaged using Oddysey® imager and Image Studio™ Lite 5.0 software (LI-COR).

(xi) Flow Cytometry

The presence of FGL2 in platelets or white blood cells was analyzed by flow cytometry. Peripheral blood samples obtained by venipuncture were collected in K3-EDTA anticoagulant and processed within 3 hours of collection. Anticoagulated venous blood was aliquoted in 100 µl amounts into 12.75 mm polypropylene tubes (Beckman coulter). Aliquots were incubated with anti-CD45 PC5 (clone J.33 Beckman Coulter) and anti-CD41 PE (clone 5B12 Dako) monoclonal antibodies at concentrations recommended by the manufacturer's directions for 20 min at room temperature in the dark. When the presence of intracellular FGL2 was sought, the cells were permeabilized using the FIX & PERM™ kit (Thermo scientific) according to the manufacturer's directions. After permeabilization, 2 µg of Alexa Fluor® 488-labeled monoclonal mouse anti-FGL2 IgG$_{2a}$ antibody (Santa Cruz Biotechnologies) or (as a negative control) Alexa Fluor® 488-labeled mouse IgG$_{2a}$ antibody (Santa Cruz) were used. When the presence of extracellular FGL2 was sought, the anti-FGL2 antibody was added without the permeabilization step. After 20 min incubation at room temperature, cells were washed twice with 5 ml PBS and resuspended in 1 ml PBS. The suspension was analyzed immediately. Labeling the antibodies with Alexa Fluor® 488 was conducted manually using the APEX™ antibody labeling kit (Invitrogen) according to manufacturer's directions. Fluorescence acquisition was performed using a Navios (Beckman Coulter) multiparameter flow cytometer. A minimum of 30,000 events were collected. Leukocytes subsets were identified by CD45/SSc plot and platelets were identified by CD41/low FSc plot. Data was analyzed using Kalusa v.1.3 or Navios v.1.3 Softwares.

(xii) Inhibition of FGL2 Activity Assay Using Anti-NPG-12 Antibody

Anti-NPG-12 IgG antibody was raised and purified form rabbits (ProteoGenix, France) according to Li et al (Li w et al., PLoS One; 9:e94551, 2014). The peptide termed NPG-12 is located at the N-terminus of human FGL2, contains 12 amino acid residues (corresponding to residues 76 to 87), and is rich in Glu. This peptide was selected as an antigenic determinant to produce antibodies in immunized rabbits. Capability and specificity of anti-NPG-12 antibody to inhibit FGL2 prothrombinase activity was validated using PC-3 extract and normal rabbit IgG as a negative control. Antibodies were incubated for 2 h at 37° C. to maximize inhibition. Briefly, cells were washed 3 times with PBS and resuspended in FXDP (Stago) to obtain a final concentration of 125×10^6 platelets/ml. Cells were lysed using sonication, divided into 400 µl aliquots and mixed with 100 µl of anti-NPG-12 antibody at various concentrations. Coagulation activity was measured immediately and after 2 h of incubation at 37° C. using an automated coagulometer as described above. Inhibition was determined by the relative change in activity at time zero and after 2 h incubation at each concentration of the antibody.

(xiii) Statistical Analysis

All data are presented as percentages or means±standard deviations. Analyses were performed using SAS® 9.4 and GraphPad Prism v.6 statistical software. The strength of the association between the sample or patient's parameters and coagulation time (see Table 1 herein) was assessed by the use of Kendall rank correlation coefficient (t). The association between platelet count and thrombin generation activity or coagulation time was assessed by Pearson's correlation coefficients (r). Statistical significance was determined using Student's t-test. P values≤0.05 were considered statistically significant.

Example 1

Dependency of Prothrombinase Activity in Plasma Free Peripheral Blood Cells (PBC) Sample on Platelet Count The purposes of this study were (i) to establish a corre- [5] lation between thrombin generation activity and coagulation activity, both mediated by FGL2, in healthy or normal subjects, i.e., subjects not inflicted with a malignant disease; and (ii) to determine the origin of the FGL2 activity.

Peripheral blood was collected from 142 subjects, includ- [10] ing healthy individuals (n=65) and hospitalized patients diagnosed with infectious diseases (n=77). For this study, patients diagnosed with malignant diseases or any other proliferative diseases backgrounds were excluded. Red blood cells were discarded and the plasma was thoroughly [15] washed out. The remaining components included white blood cells and platelets. Samples were aliquoted to include similar counts of mononuclear cells (ca. $1.5 \times 10^6$). The samples were tested for prothrombinase activity by either coagulation time or thrombin generation as described in [20] Materials and Methods. Coagulation time measurement is a simpler and straightforward method for estimation of prothrombinase activity as compared to thrombin generation assay.

As shown in FIG. 1A and Table 1, the coagulation time [25] was found to inversely correlate with thrombin generation with high significance (t=−0.38, p-value<0.0001), exhibited by an overall linear correlation (r=−0.64), confirming that the two methods measure different products resulting from the same activity.

Figure 1B:
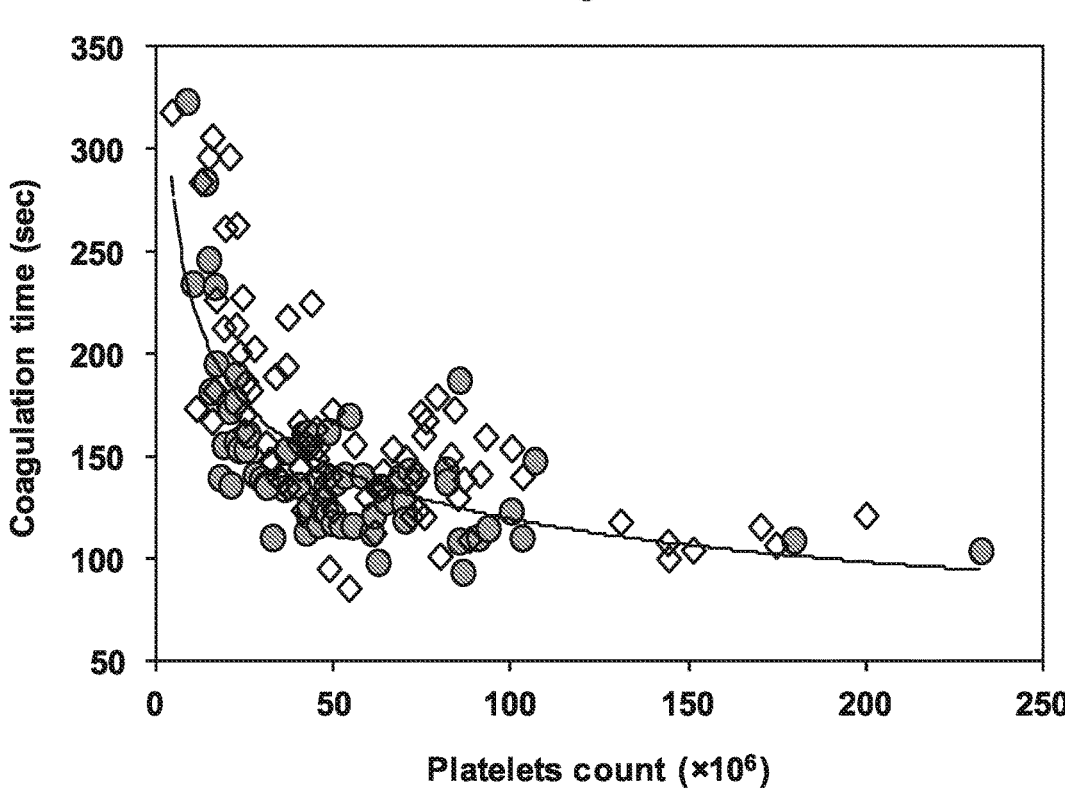

To determine the origin of the prothrombinase activity in the tested samples, possible correlations between the measured activity and a range of parameters, including blood cell counts and subject characteristics, were examined. As seen in Table 1 and FIG. 1B, a notable correlation was detected between the platelet count in the sample and coagulation time (t=−0.47, p-value <0.0001), exhibited by a strong power-regression correlation (r=−0.72) (FIG. 1B). No other notable correlations were detected.

FIG. 1B implies that coagulation activity level of FGL2 is optimal for platelet count $\geq 50 \times 10^6$ cells/ml, ideally $100 \times 10^6$, in order to be near the plateau and off the steep region of the slope of the curve.

Figure 2A:
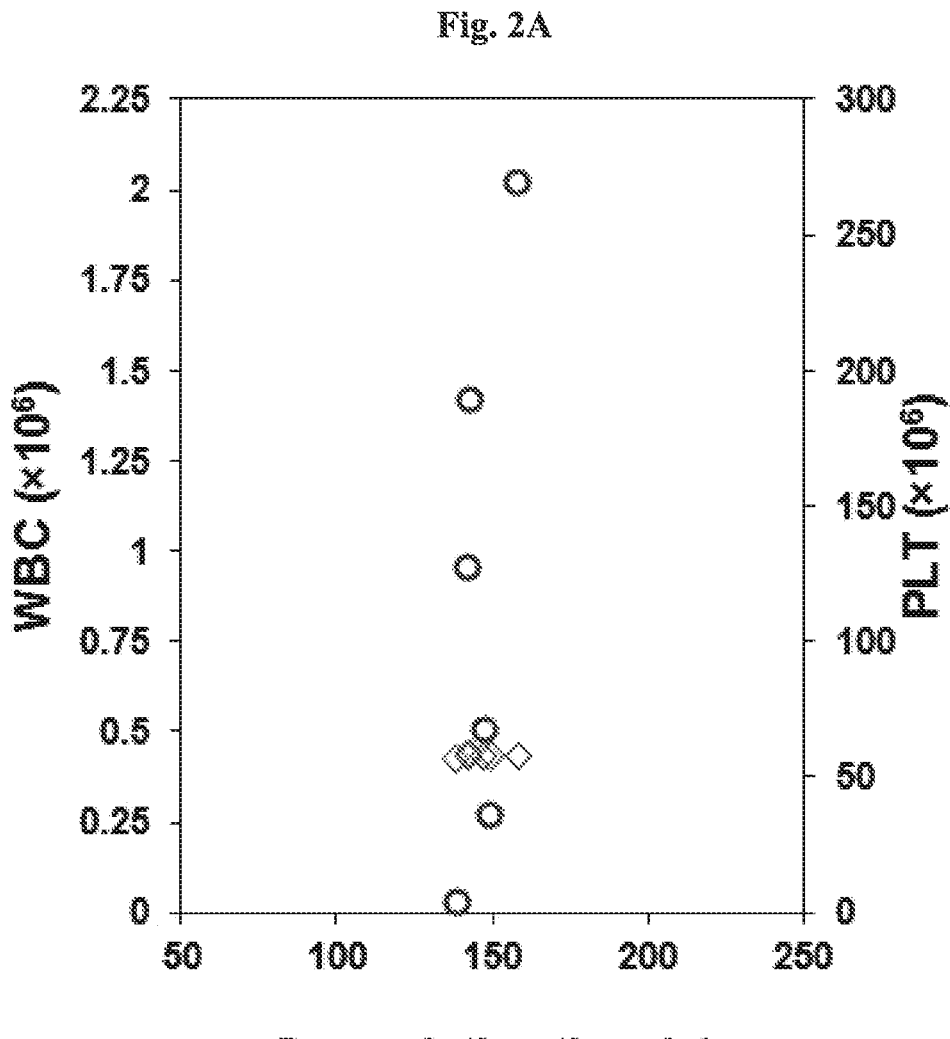
FIGS. 2A-2B are graphs showing correlation between prothrombinase activity, platelets ($\diamond$) and white blood cells ($\circ$) counts. Coagulation time was measured n separately purified platelets and white blood cells from a single donor.
Figure 2B:
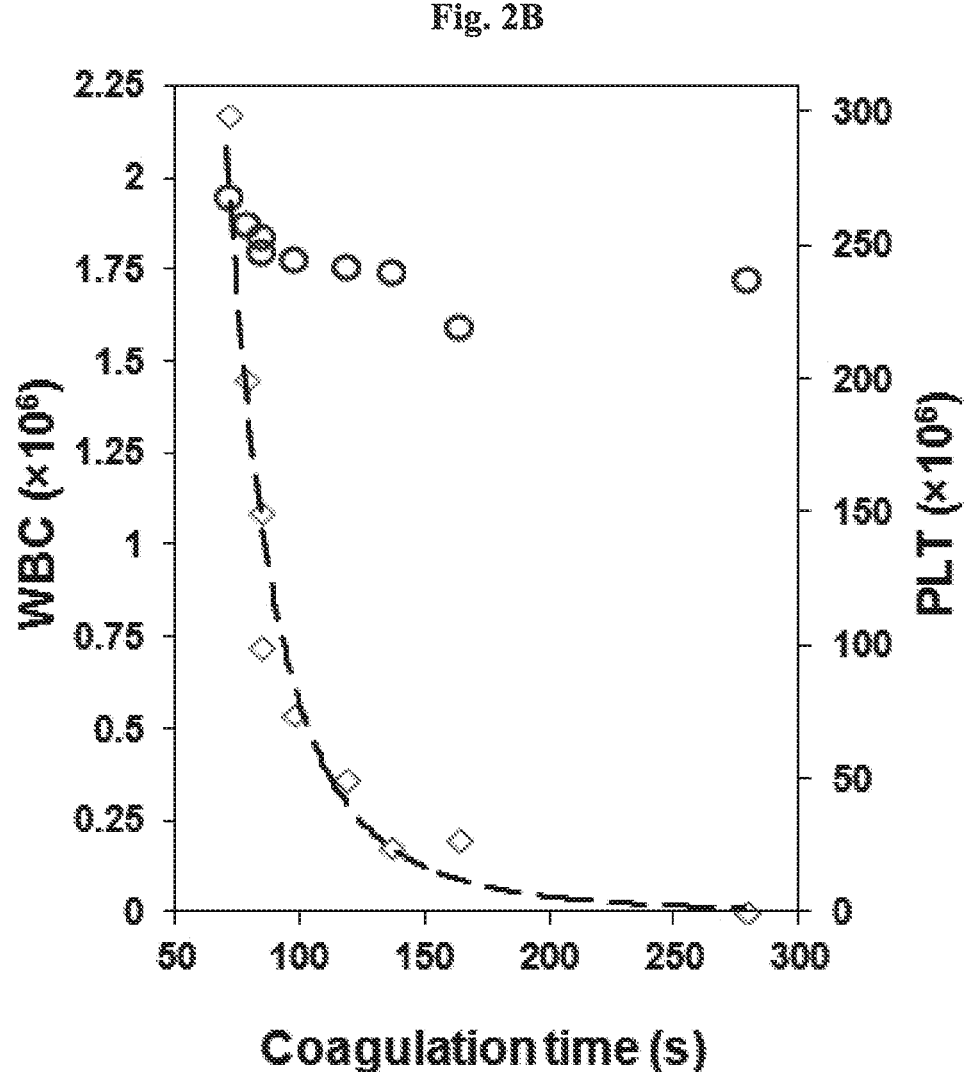

To validate this finding, samples prepared from a single donor were reconstituted to include similar amounts of platelets with a gradient of white blood cells (WBCs) (FIG. 2A), and vise verse, namely, samples containing similar amounts of WBCs and a gradient of platelets (FIG. 2B). Importantly, in agreement with the multiple sample observation (FIG. 1B), coagulation time showed a complete dependency on the count of platelets in the sample, but did not correlate with, or depended on the count of WBCs.

TABLE 1

| | | | | | |
|---|---|---|---|---|---|
| Study population and analysis of correlation coefficient | | | | | |
| | | | | Hospitalized | |
| | All subjects | Healthy | Total | Bacterial infections | Viral infections |
| Number | 142 | 65 | 77 | 47 | 30 |
| Gender, male/female | 91/51 | 44/21 | 47/30 | 28/19 | 19/11 |
| Age, median (range) | 61 (22-95) | 55 (23-74) | 66 (22-95) | 66 (23-88) | 69 (22-95) |
| Correlation coefficient (τ) between coagulation time and: | | | | | |
| Thrombin generation activity | −0.381*** | −0.44*** | −0.369* | | |
| Age | 0.067 | 0.075 | −0.039 | | |
| Prothrombin Time (PT) | n/a | n/a | 0.007 | | |
| Partial thromboplastin time (PTT) | n/a | n/a | 0.051 | | |
| Platelets | −0.474*** | −0.493*** | −0.521*** | | |
| White blood cells (total) | 0.137 | −0.106 | 0.218* | | |
| Neutrophils | 0.168* | 0 | 0.210* | | |
| Lymphocytes | −0.166* | −0.093 | −0.149 | | |
| Monocytes | 0.129 | −0.038 | 0.135 | | |
| Eosinophils | 0.096 | 0.049 | 0.082 | | |
| Basophils | 0.08 | −0.035 | 0.214 | | |

***p-value < 0.0001

*p-value < 0.01

Example 2

Assessment of FGL2-Mediated Coagulation in Plasma Free PBC Extracts

In order to rule out the possibility that prothrombin or traces of thrombin in the samples had actually driven the coagulation process (rather than FGL2), a pool of PBC samples (containing WBC and platelets) was lysed in factor-II deficient plasma (FIIDP) and tested for its ability to shorten coagulation time.

Figure 3:
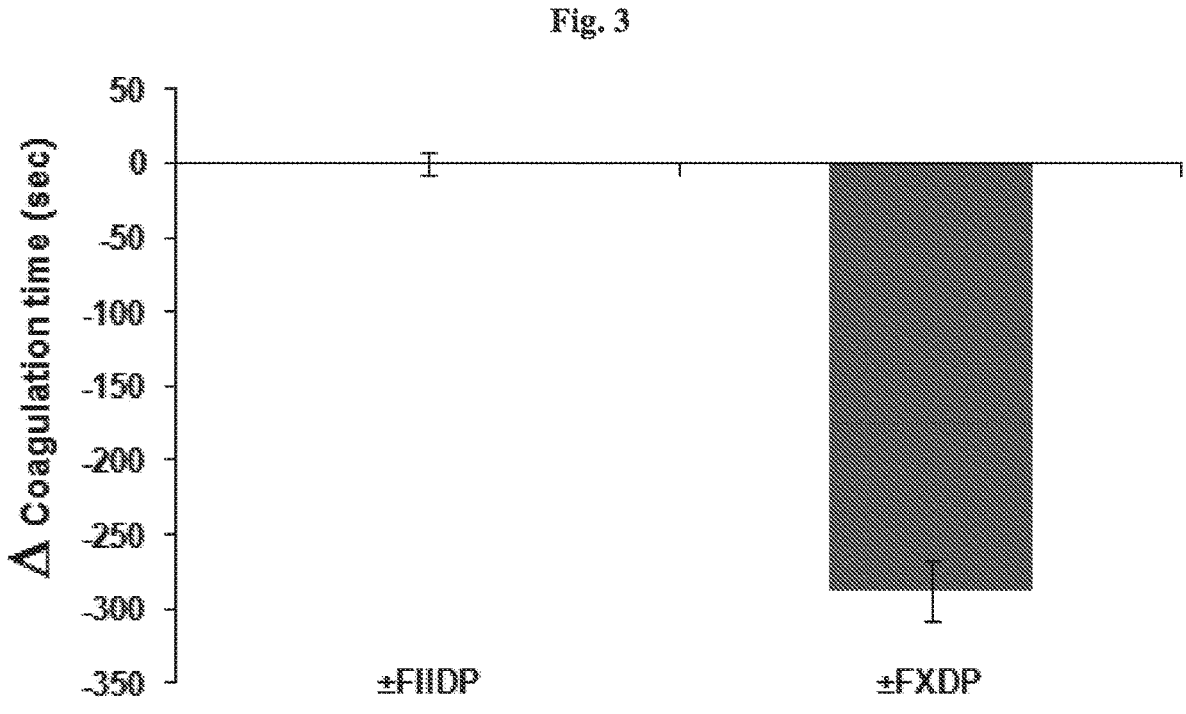
FIG. 3 is a bar graph showing coagulation mediated through prothrombinase activity in plasma-free peripheral blood cells (PBC) samples extracts (containing both white blood cells and platelets). Y axis denotes the difference (A) in coagulation time in the presence and absence of PBC in factor X deficient plasma (FXDP), and in the presence and absence of PBC in factor II deficient plasma (FIIDP). The measurements were performed in quadruplicates. Error bars represent standard deviation.

As shown in FIG. 3, while PBC extract in FXDP shortened the coagulation time by 288±20 seconds, PBC extract in FIIDP failed to shorten coagulation time (Δ=0±8 seconds). Coagulation time differences in the presence and absence of PBC in FXDP was 109 and 397 seconds, respectively, whereas coagulation time in the presence and absence of PBC in FIIDP was identical (97 seconds).

Figure 4A:
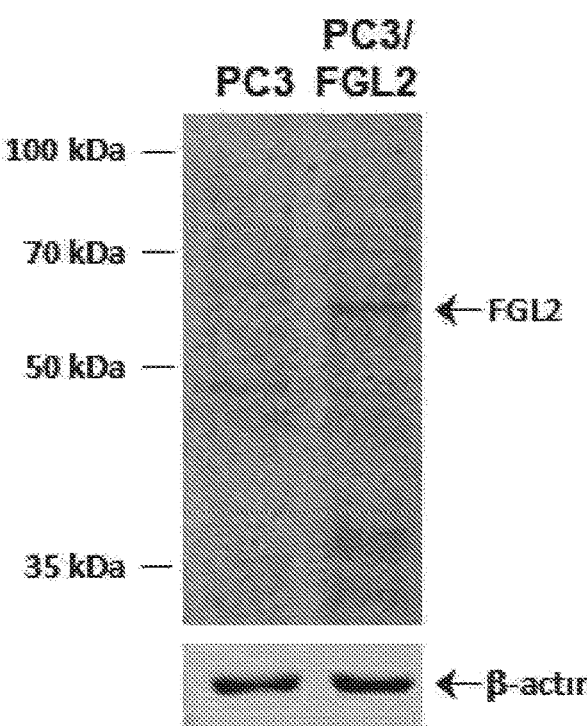
FIG. 4A-4B describe FGL2 prothrombinase overexpressing PC3 cell line extracts and coagulation mediated thereby.
Figure 4B:
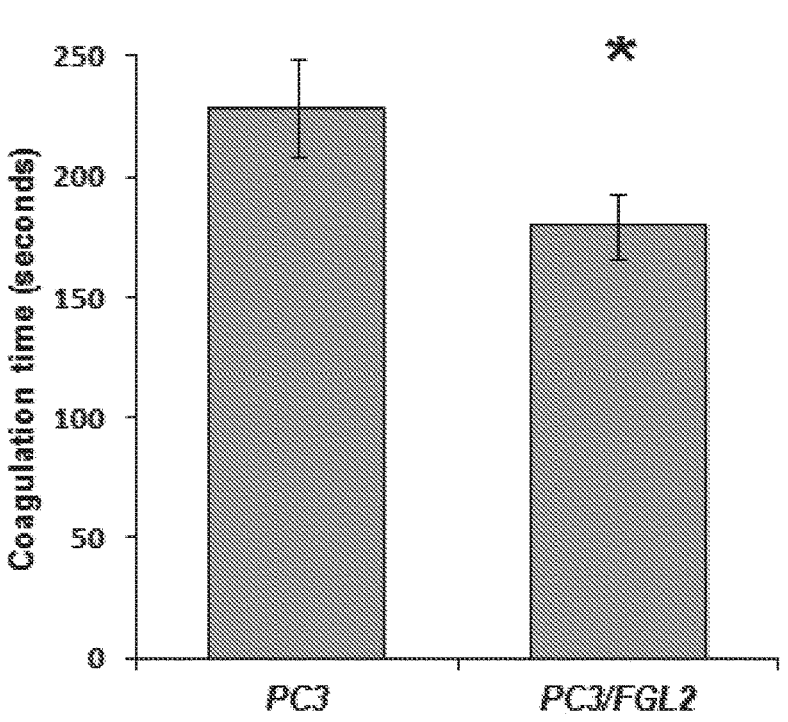

To confirm that FGL2 can indubitably induce coagulation time shortening in FXDP, PC-3 cell line overexpressing FGL2 was prepared as described in Materials and Methods (see FIG. 4A). As shown in FIG. 4B, in cells overexpressing FGL2, coagulation time was significantly shortened as compared to FGL2 wild type cells. These results confirmed that prothrombinase activity (rather than fibrinogenase) was measured in the samples.

Example 3

Assessment of FGL2 and Factor X in Plasma Free Peripheral Blood Cells

Two major prothrombinases are recognized: Factor Xa and FGL2 (Levy et al., *Am. J. Pathol.*, 156:1217-1225, 2000; Schenone et al., *Curr Opin Hematol.*, 11:272-277, 2004). To determine the identity of the active prothrombinase in the studies described in Examples 1 and 2 above, an immunoprecipitation technique was applied to detect Factor X or FGL2 in a pool of samples. Accordingly, identical PBC samples were extracted and exposed to immobilized anti-FGL2 or anti-FX IgG antibodies as well as matched IgG subclasses as a control, as described in Materials and Methods. The immunoprecipitated proteins were analyzed by western blot.

Figure 5:
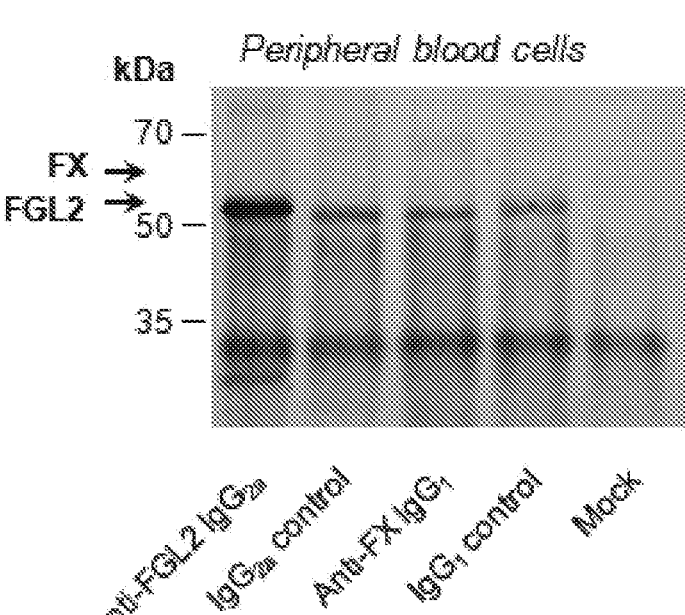
FIG. 5 is a Western blot analysis of immunoprecipitated FGL2 and factor X (FX) from plasma-free PBC. Identical samples were immunoprecipitated by protein A/G-agarose beads using anti-FGL2 or anti-FX IgG or matched normal IgG subclasses as controls (indicated below each SDS-PAGE lane). Mock represents nonspecific binding. Expected FX and FGL2 protein are indicated by arrows.

As shown in FIG. 5, FGL2 was readily precipitated from PBC, as previously reported by Marazzi et. al. (Marazzi et al., *J. Immunol.*, 161:138-147, 1998), however, FX was not detected.

Example 4

Detection of FGL2 in Platelets

To examine whether FGL2 is found in platelets, platelets were washed and purified from fresh blood samples by series of centrifugations as described in Materials and Methods. To assure the purity of the sample, absence of leukocytes was confirmed using a sensitive blood cell counter (detection limit of ≤2 cells/µl, using Sysmex® XN-1000™ automatic blood cell counter). The platelets were kept non-activated throughout the separation process using CTAD solution (mixture of citrate, theophylline, dipyridamole and adenosine (see Ahnadi et al., *Thromb. Haemost.* 90:940-948, 2003). Detection of FGL2 was carried out by immunoprecipitation as described in Materials and Methods. Briefly, identical samples were immunoprecipitated by protein A/G-agarose beads using anti-FGL2 or anti-FX IgG or matched normal IgG subclasses as controls. Mock represented non-specific binding to protein A/G-agarose beads.

Figure 6A:
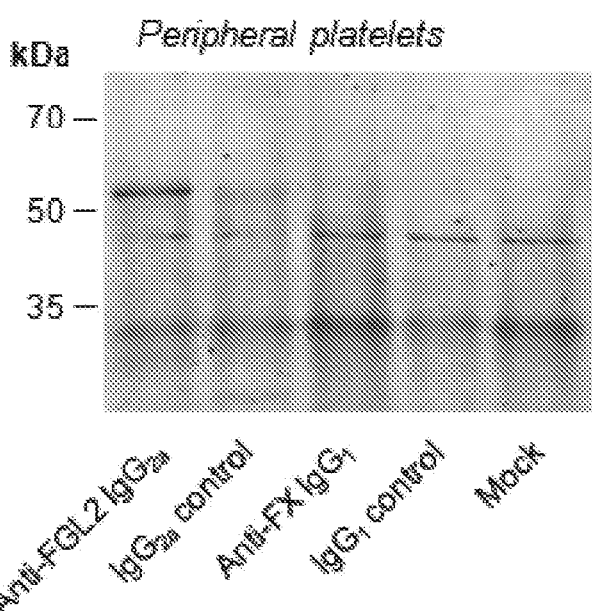
FIGS. 6A-6B are Western blot analyzes of immunoprecipitated FGL2 and FX from pure platelet extracts (plasma-free) (6A), and from platelets cytosol and membrane fractions (6B). Identical samples were immunoprecipitated by protein A/G-agarose beads using anti-FGL2 or anti-FX IgG or matched normal IgG subclasses as controls (indicated below each SDS-PAGE lane). Mock represents nonspecific binding. Expected FGL2 protein sizes are indicated by arrows.

As shown in FIG. 6A, FGL2 was clearly precipitated from platelets, while factor X could not be detected.

To determine the localization of FGL2 in platelets, platelets membrane-associated and soluble proteins were further isolated and analyzed by western blotting.

Figure 6B:
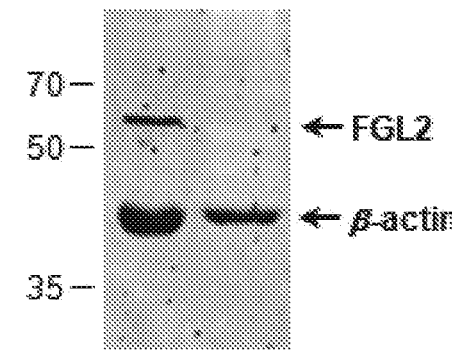

As shown in FIG. 6B, FGL2 was predominantly detected in the soluble fraction (cytosol) rather than within the membrane fraction.

The presence of FGL2 in platelets was further confirmed by flow cytometry in whole blood with or without permeabilization. The fluorescence intensity of IgG control-Alexa Fluor® 488 or FGL2-Alexa Fluor® 488 antibodies was detected in gated platelet using log SSC/FSC/CD41$^+$ or in gated lymphocyte using CD45$^+$/SSC plot following cell permeabilization or intact cells. As shown in FIGS. 7A and 7C, FGL2 protein was detected after permeabilization in lymphocytes and in platelets. However, as shown in FIGS. 7B and 7D, FGL2 could not be detected without permeabilization. Taken together, these results support the finding that FGL2 is predominantly stored intracellularly in resting platelets and lymphocytes.

Example 5

Evaluation of FGL2 in Megakaryoblastic Cells

To gain insight into the origin of FGL2 in platelets, the presence of FGL2 in a megakaryoblastic cell line, CMK was tested. The CMK line was established from the peripheral blood of a megakaryoblastic leukemia patient. Total protein and RNA were extracted from the CMK cell line. Extracts were reduced and separated on SDS-PAGE as describe in Materials and Methods. Presence of FGL2 and β-actin was analyzed by western blotting.

Figure 8:
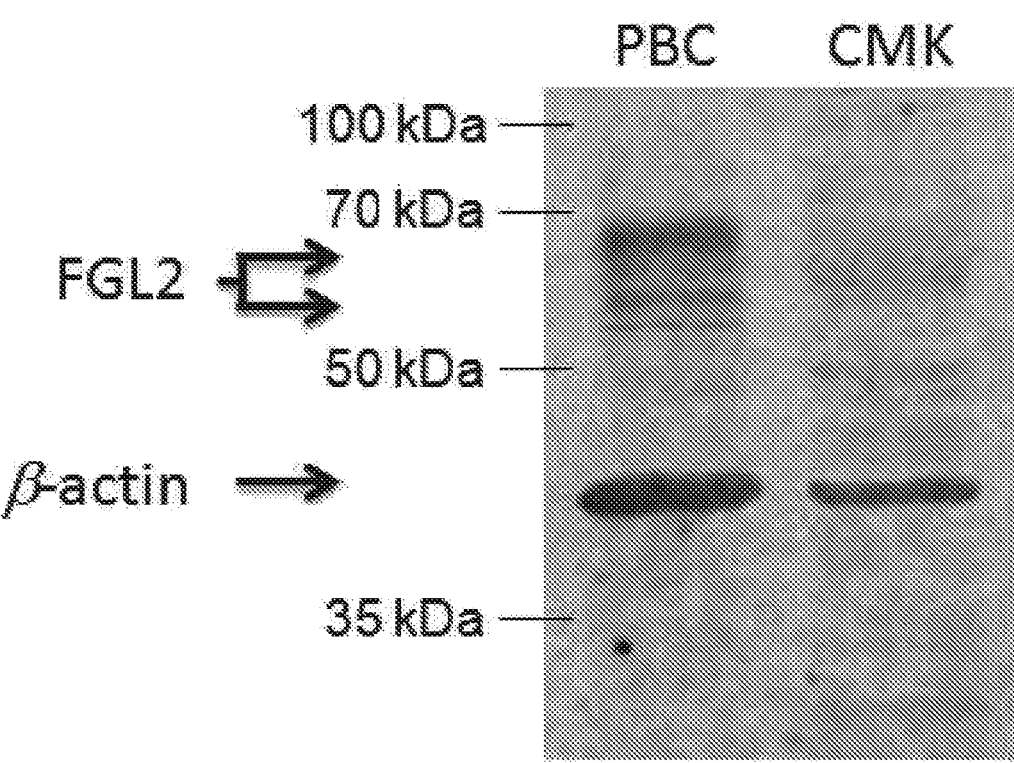
FIG. 8 is a Western blot analysis of FGL2 and β-actin expression in PBC and Megakeryoblast cell line (CMK) extracts. Extracts were reduced and separated on SDS-PAGE.

Immunoblotting analyzes showed no trace of FGL2 in megakaryoblasts, as seen in FIG. 8. Similarly, no evidence for FGL2 message RNA was found using real-time PCR (data not shown).

Example 6

Evaluation of Platelet FGL2 as a Potent Procoagulant

Figure 9:
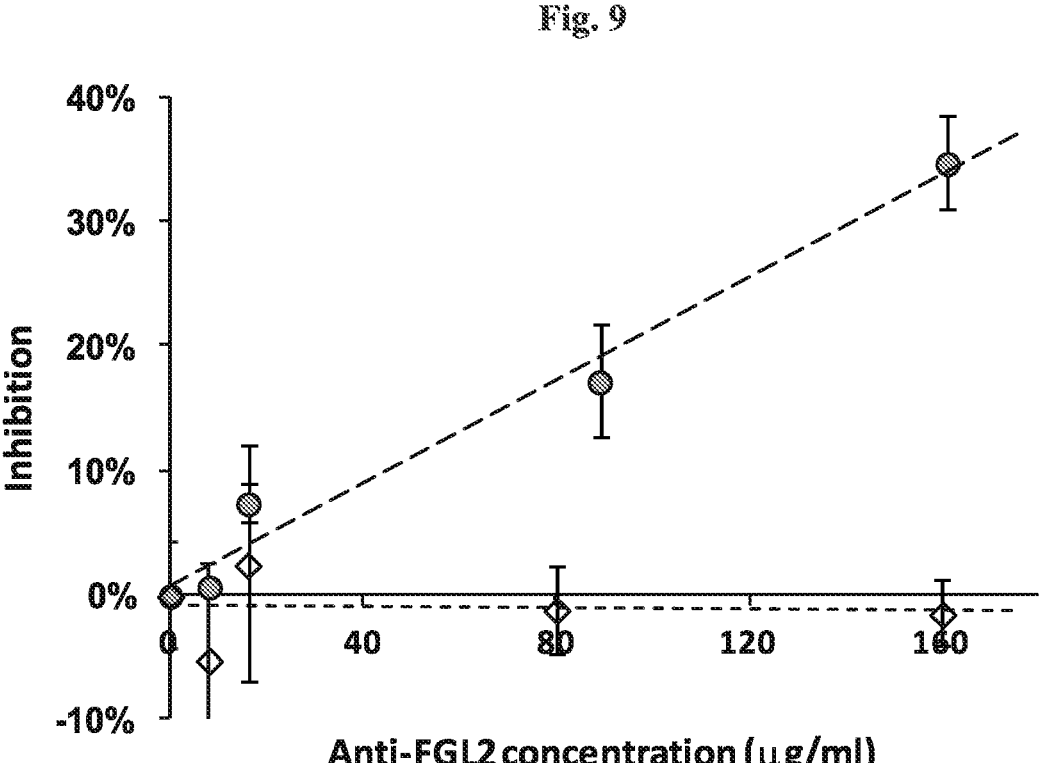
FIG. 9 is a graph showing inhibition of coagulation induced by plasma-free PBC extracts using anti-NPG-12 antibody. A pool of PBC was incubated with increasing concentrations of rabbit anti-NPG-12 antibody (full circles) capable of specifically inhibiting FGL2 prothrombinase activity. Normal Rabbit IgG was used as a control (empty rhombuses). The resultant inhibition is expressed in percentages. Inhibition is calculated as a ratio between measured activities in the presence and absence of antibody. Error bars represent standard deviation. Dashed lines represent linear trend of inhibition.

A previous study reported the development of an antibody directed against the N-terminal glutamate-rich region of FGL2 that is capable of inhibiting FGL2 prothrombinase activity (see Li et al., *PLoS One* 9:e94551, 2014). This antibody, designated as anti-NPG-12 antibody, was reported to inhibit FGL2 activity by 30% (at 100 µg/ml) in human umbilical vein endothelial cells (HUVECs). To validate that the observed prothrombinase activity in PBC is exerted by FGL2, a direct inhibition was tested. A pool of PBC was incubated with increasing concentrations (up to 160 µg/ml) of rabbit anti-NPG-12 antibody capable of specifically inhibiting FGL2 prothrombinase activity, as described in Materials and Methods. Normal Rabbit IgG was used as a control. As a result, and as shown in FIG. 9, clotting time was elongated in correlation with antibody concentration, leading to 35% decrease in activity (p<0.05), reinforcing the role of FGL2 in the observed procoagulant activity.

Example 7

Diagnosing Mycosis Fungoides (MF) Using Platelet-Mediated FGL2 Activity

Dermal mycosis fungoides (MF), a common form of cutaneous T-cell lymphoma, has been quite difficult to diagnose to date. The symptoms of MF typically mimic those of psoriasis and dermatitis, therefore thwarting efficient diagnosis. Current diagnosis depends highly on the visual skills of the attending physician and laboratory technician in recognizing the manifestations of the rash, and of the cell tissue biopsy.

Platelet-mediated FGL2 activity, serving as an assay for rapid and definitive biochemical diagnosis of MF, was applied to blood samples obtained from early and late MF (22 patients), 22 patients with psoriasis and other dermatitis, and control (healthy subjects, n=19).

Figure 10:
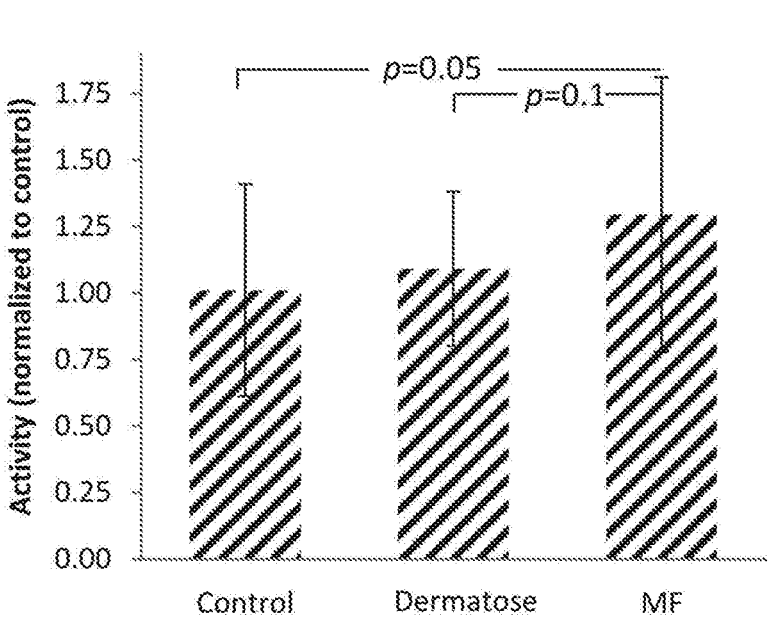
FIG. 10 is a bar graph showing platelet-mediated FGL2 coagulation activity as determined in peripheral blood samples (containing white blood cells and platelets) of mycosis fungoides (MF) patients (n=22), dermatoses patients (n=22, psoriasis and other dermatitis) and healthy controls (n=19). The samples were adjusted to equal number of platelets ($100 \times 10^6$)

As shown in FIG. 10, FGL2 activity level was elevated in blood samples obtained from MF patients in comparison to activity level of dermatoses patients (such as psoriasis and other dermatitis) and compared to that of healthy controls. Thus, while FGL2 activity levels in normal (control) and in dermatoses (after normalized to control) patients was 1.01 and 1.09, respectively, MF patients presented a substantially higher level of coagulation activity of 1.30 (normalized to control). These findings correlated with FGL2 mRNA levels in the blood and FGL2 activity measured in PBMC thrombin generation assays (results not shown).

The platelets assay afforded measuring the coagulation time in an automated manner, as an indication of the level of activity of FGL2. The assay is inexpensive, rapid and can be mass-produced in a laboratory setting (thus suited for hospitals and diagnostic laboratories) and is most suited as a biochemical assay for diagnosis of multitude malignant diseases and disorders.

Example 8

Correlation Between Platelet-Mediated FGL2 Activity and PET Scanning

Feasibility of follow-up or monitoring the therapy of a malignant disease using a contemplated diagnosis method was assessed by comparing platelet-mediated FGL2 activity in patients diagnosed with aggressive lymphoma to PET scans obtained from these patients in the course of anti-cancer treatment protocols.

Application of monitoring of FGL2 activity in platelets for disease state follow up in individual patients was conducted as follows:

In seven patients, platelet-mediated FGL2 activity was determined (as described in Materials and Methods) in approximate to disease state diagnosis by PET scan. To compare variations in FGL2 activity during follow up, the activity determined during active disease/relapse was set to 100%. Rest of activities determined for the same patients were normalized accordingly. In one patient ("+"), activity was available 17 month prior the diagnosis of the disease. Platelet-mediated FGL2 activity was assessed in between PET scanning episodes.

Figure 11:
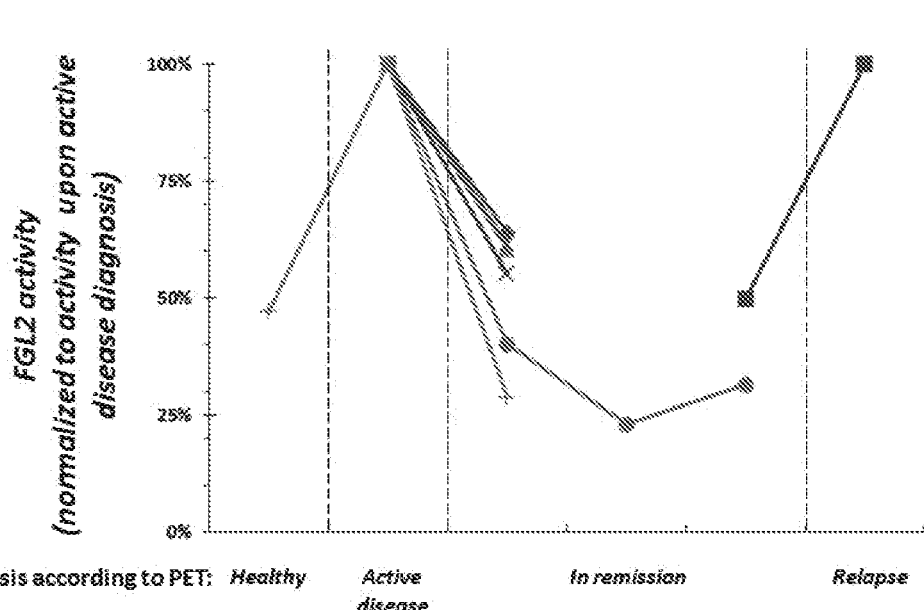
FIG. 11 is a graph showing the correlation between FGL2 activity and diagnosis according to positron emission tomography (PET) scanning at various stages of aggressive lymphoma diagnosed in 7 patients.

As shown FIG. 11, FGL2 activity correlated well with disease stage as diagnosed by PET. Moreover, platelet-mediated FGL2 activity measured in remission period when no PET scan was conducted or could be conducted, was able to indicate relapse/failure of treatment before it was observed in PET scans, thus providing straight forward and earlier indication of disease stage.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A kit for diagnosis, follow-up or prognosis of a malignant proliferative disease or disorder, the kit comprising: (a) means for measuring platelet-mediated FGL2 activity level in a biological sample containing platelets of a subject to be tested; said means comprising (1) factor X deficient plasma; (2) tissue factor or an artificial tissue factor surrogate; (3) FGL2 activity level predetermined calibration curve; (b) instructions for measuring platelet-mediated FGL2 activity level in said sample comprising measuring coagulation time of said sample being suspended in said factor X deficient plasma and transforming coagulation time into FGL2 activity level using said predetermined calibration curve; and, optionally, (c) at least one means for collecting a biological sample containing platelets of a subject to be tested; and/or (d) at least one control sample.

2. The kit according to claim 1, designed for assessing platelet-mediated FGL2 coagulation activity level.

3. The kit according to claim 1, designed for assessing platelet-mediated FGL2 units or thrombin concentration.

4. The kit according to claim 1, comprising FGL2 substrate.

5. The kit according to claim 1, comprising FGL2 substrate prothrombin, an active segment thereof, a derivative thereof, a homolog thereof, or any chromogenic substrate suitable for the determination of serine proteases.

6. The kit according to claim 1, comprising Factor X deficient plasma (FXDP), calcium and optionally phospholipids.

7. The kit according to claim 1, further comprising at least one of a buffer, a detectable moiety, an enzyme substrate, a color reagent and any combinations thereof.

8. The kit according to claim 1, comprising means for collecting a sample to be tested.

9. The kit according to claim 1, wherein the control sample is platelet-mediated FGL2 activity sample in a subject not affected by a malignant proliferative disease.

10. The kit according to claim 1, wherein said platelet-mediated FGL2 level is activity is fibrin formation or coagulation induced by addition of Factor X deficient plasma (FXDP) and tissue factor.

11. The kit according to claim 1, wherein said platelet-mediated FGL2 activity level is thrombin generation or prothrombinase activity induced by addition of an FGL2 prothrombinase substrate.

12. The kit according to claim 1, wherein said biological sample is pure platelets, a platelet-rich plasma (PRP) or peripheral blood cells (PBC) supplemented with platelets obtained from the subject.

13. The kit according to claim 1, wherein said malignant proliferative disease or disorder is a solid tumor or a non-solid tumor of circulating cells.

14. The kit according to claim 1, wherein said malignant proliferative disease or disorder is selected from mycosis fungoides pancreatic cancer, breast cancer, squamous cell carcinoma, multiple myeloma, prostate cancer, Langerhans cell sarcoma, thyroid papillary cancer, esophageal cancer, endometrial sarcoma, mammary gland cancer, mediastinal large cell lymphoma, Hodgkin lymphoma, small cell lung cancer or non-small-cell lung carcinoma, kidney cancer, uterus cancer, bladder cancer, colon cancer, ovarian cancer, mixed tumors of salivary gland, tumors in lip and oral cavity, carcinoma of the eyelid and carcinoma of the conjunctiva, pharynx cancer, larynx cancer, paranasal sinuses cancer, adenomas, adenocarcinomas, sarcomas, Ewing's tumor, testicular cancer, retinoblastoma, Wilms' tumor, neuroblastoma, mesothelioma, skin cancer, malignant melanomas, carcinoma of the lacrimal gland, sarcoma of the orbit, brain cancer, spinal cord cancer, vascular system cancer, hemangiosarcoma, malignant lymphoma, Kaposi's sarcoma, mycosis fungoides, Sézary syndrome, myeloid leukemia, chronic myelogenous leukemia, acute myelogenous leukemia, acute myelogenous leukemia with maturation, acute promyelocytic leukemia, acute non-lymphocytic leukemia, acute non-lymphocytic leukemia with increased basophils, acute monocytic leukemia, acute myelomonocytic leukemia with eosinophilia, lymphocytic leukemia, and myelo-proliferative diseases.

15. The kit according to claim 1, wherein said malignant proliferative disease or disorder is mycosis fungoides (MF) and the Sézary syndrome.

16. The kit according to claim 1, wherein said malignant proliferative disease or disorder is a solid tumor or a hematological malignancy.

* * * * *